(12) United States Patent
Karlsson-Parra et al.

(10) Patent No.: US 9,476,028 B2
(45) Date of Patent: *Oct. 25, 2016

(54) METHOD FOR PROLIFERATION OF ANTIGEN-SPECIFIC T CELLS

(75) Inventors: Alex Karlsson-Parra, Uppsala (SE); Anna-Carin Wallgren, Uppsala (SE); Bengt Andersson, Mölndal (SE)

(73) Assignee: IMMUNICUM AB, Gothenburg (SE)

( * ) Notice: Subject to any disclaimer, the term of this patent is extended or adjusted under 35 U.S.C. 154(b) by 212 days.

This patent is subject to a terminal disclaimer.

(21) Appl. No.: 14/110,901

(22) PCT Filed: Apr. 12, 2012

(86) PCT No.: PCT/EP2012/056661
§ 371 (c)(1),
(2), (4) Date: Dec. 18, 2013

(87) PCT Pub. No.: WO2012/140130
PCT Pub. Date: Oct. 18, 2012

(65) Prior Publication Data
US 2014/0112956 A1    Apr. 24, 2014

Related U.S. Application Data

(60) Provisional application No. 61/474,904, filed on Apr. 13, 2011.

(51) Int. Cl.
| | | |
|---|---|---|
| *C12N 5/00* | (2006.01) | |
| *C12N 5/02* | (2006.01) | |
| *A61K 38/00* | (2006.01) | |
| *A61K 39/00* | (2006.01) | |
| *C12N 5/0783* | (2010.01) | |
| *A61K 35/17* | (2015.01) | |
| *C12N 5/0784* | (2010.01) | |

(52) U.S. Cl.
CPC ............. *C12N 5/0636* (2013.01); *A61K 35/17* (2013.01); *A61K 39/0011* (2013.01); *C12N 5/0639* (2013.01); *A61K 2039/5156* (2013.01); *C12N 2500/40* (2013.01); *C12N 2501/22* (2013.01); *C12N 2501/2301* (2013.01); *C12N 2501/2302* (2013.01); *C12N 2501/2304* (2013.01); *C12N 2501/2315* (2013.01); *C12N 2501/24* (2013.01); *C12N 2501/25* (2013.01); *C12N 2501/515* (2013.01); *C12N 2502/11* (2013.01)

(58) Field of Classification Search
None
See application file for complete search history.

(56) References Cited

U.S. PATENT DOCUMENTS

| | | | |
|---|---|---|---|
| 5,827,642 A | 10/1998 | Riddell et al. | |
| 6,274,378 B1 * | 8/2001 | Steinman | C12N 5/0639 435/325 |
| 6,821,778 B1 * | 11/2004 | Engleman | C12N 5/0636 435/372 |
| 9,211,321 B2 * | 12/2015 | Karlsson-Parra | A61K 39/0011 |

FOREIGN PATENT DOCUMENTS

WO    2006/065495 A2    6/2006

OTHER PUBLICATIONS

Stuber et al. ( Cancer Immunol, 1990, v.31, pp. 76-80).*
Tumeh et al., The impact of ex vivo clinical grade activation protocols on human T cell phenotype and function for the generation of genetically modified cells for adoptive cell transfer therapy, J Immunother, 33(8):759-768 (Oct. 2010).
Wallgren et al., Direct Allorecognition Promotes Activation of Bystander Dendritic Cells and Licenses Them for Th1 Priming: A Functional Link Between Direct and Indirect Allosensitization, Scandinavian Journal of Immunology, 62:234-242 (2005).
Gustafsson et al., Recruitment and Activation of Natural Killer Cells In vitro by a Human Dendritic Cell Vaccine, American Association for Cancer Research, 68:(14) (Jul. 15, 2008).
Yang et al., A Simplified Method for the Clinical-scale Generation of Central Memory-like CD8+ T Cells After Transduction With Lentiviral Vectors Encoding Antitumor Antigen T-cell Receptors, J Immunother, 33(6):648-658 (2010).
Ho et al., In vitro methods for generating CD8+ T-cell clones for immunotherapy from the naive repertoire, Journal of Immunological Methods, 310:40-52 (2006).
Gattinoni et al., Acquisition of full effector function in vitro paradoxically impairs the in vivo antitumor efficacy of adoptively transferred CD8+ T cells, The Journal of Clinical Investigation, 115(6):1616-1626 (2005).
Gritzapis et al., Identification of a Novel Immunogenic HLA-A*0201-Binding Epitope of HER-2/neu with Potent Antitumor Properties, The Journal of Immunology, 181:146-154 (2008).
Murphy et al., Gene Modification Strategies to Induce Tumor Immunity, Immunity, 22:403-414 (Apr. 2005).
Robbins et al., Cutting Edge: Persistence of Transferred Lymphocyte Clonotypes Correlates with Cancer Regression in Patients Receiving Cell Transfer Therapy, The Journal of Immunology, 173:7125-7130 (2004).
Mailliard et al., alpha-Type-1 Polarized Dendritic Cells: A Novel Immunization Tool with Optimized CTL-inducing Activity, Cancer Research, 64:5934-5937 (2004).
Powell et al., Transition of late-stage effector T cells to CD27+ CD28+ tumor-reactive effector memory T cells in humans after adoptive cell transfer therapy, Blood Journal, 105:241-250 (2005).
Chang et al., Phase II Trial of Autologous Tumor Vaccination, Anti-CD3-Activated Vaccine-Primed Lymphocrytes, and Interleukin-2 in Stage IV Renal Cell Cancer, Journal of Clinical Oncology, vol. 21, No. 5, pp. 884-890 (Mar. 1, 2003).
Jordan et al., Optimal analysis of composite cytokine responses during alloreactivity, Journal of Immunological Methods, 260:1-14 (2002).

(Continued)

*Primary Examiner* — Michail Belyavskyi
(74) *Attorney, Agent, or Firm* — Porter Wright Morris & Arthur LLP

(57) ABSTRACT

The present invention relates to an in vitro method for priming genetically modified T cells suitable for administration to a patient having a tumor. The invention is also directed to the composition obtained by the method and uses thereof.

13 Claims, 22 Drawing Sheets

(56) References Cited

OTHER PUBLICATIONS

Sadelain et al., Targeting Tumours with Genetically Enhanced T Lymphocytes, Nature Reviews, Cancer, 3:35-45 (Jan. 2003).

Vera et al., Immunotherapy of Human Cancers Using Gene Modified T Lymphocytes, Curr Gene Ther., 9(5):396-408 (Oct. 2009).

Fu et al., A Simple and Sensitive Method for Measuring Tumor-Specific T Cell Cytotoxicity, PLoS ONE, vol. 5, Issue 7, e11867 (Jul. 29, 2010).

* cited by examiner

Cont. Figure 6
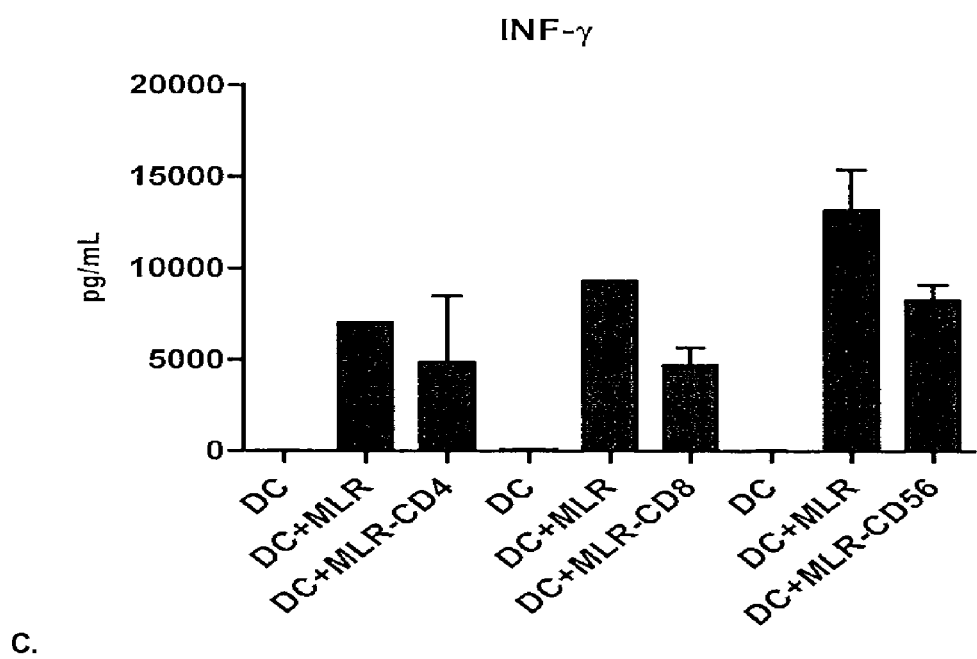
C.

METHOD FOR PROLIFERATION OF ANTIGEN-SPECIFIC T CELLS

TECHNICAL FIELD

The present invention relates to the field of immunology and cancer therapy and more specifically to a method of activation of genetically modified antigen specific T cells and the genetically modified T cells produced by said method.

BACKGROUND

T cells recognize tumors or infected cells and prevent onset of disease by killing these target cells. However, the interplay of tumors or pathogens and the immune system is complex, as demonstrated by cancer or chronic infections developing in the presence of specific T cells, whereby the pathogens or tumors obviously could evade T-cell surveillance.

The ability of T cells to detect virtually any pathogenic invader is granted by its extraordinarily diverse receptor repertoire, which allows the T-cell pool to recognize a vast number of peptides upon presentation by major histocompatibility complex (MHC) molecules. Still, signaling through the T-cell receptor (TCR) (signal 1) is not sufficient for adequate T-cell activation, as costimulatory molecules provide indispensable signals for proliferation, survival, and differentiation (signal 2). In fact, naive T cells that only receive signal 1 without signal 2 are rendered anergic (unresponsive) or die through apoptosis. The integration of signals 1 and 2 is required for full T-cell activation, and the strength of these signals shapes the size of the ensuing T-cell pool. Moreover, full differentiation into effector T cells is generally dependent on a third signal, which is supplied by the antigen-presenting cell (APC) in soluble form and provides instructive signals for the type of effector T cell that is required. This 'three-signal' concept depicts a model for the activation of naive T cells and the subsequent formation of effector T cells. Yet, the immune system provides a plethora of diverse costimulatory molecules and these various types of signal 2 and 3 all contribute in their own unique manner to the quality of the T-cell response. Costimulatory signals and soluble forms of signal 3 can act on particular aspects of T-cell activation, such as survival, cell cycle progression, type of effector cell to be developed, and differentiation to either effector or memory cell.

It is now generally accepted that mature antigen-presenting dendritic cells (DCs) have to be "helped" by other lymphocytes, including CD4+ T cells NK cells and NKT cells, in order to induce long-lived memory CD8+ T cells. This "help" induces the mature DCs to differentiate further, a process known as licensing. "Helper" signals has multiple effects on DCs, including the upregulation of costimulatory molecules, the secretion of cytokines, and the upregulation of several antiapoptotic molecules, all of which cumulatively potentiate the ability of DCs to optimally activate cognate T cells, especially CD8+ T cells. Moreover, "helper" lymphocytes may also express or secrete factors that directly affect T cell survival, cell cycle progression, type of effector cell to be developed, and differentiation to either effector or memory cell.

One strategy for fighting chronic infections or aggressive cancer is adoptive T-cell therapy, which involves the transfer of effector T cells to restore specific T-cell responses in the host. Recent technical developments to obtain T cells of wanted specificities have created increasing interest in using adoptive T-cell therapy in different clinical settings. Adoptive cell transfer therapy is the administration of ex vivo activated and expanded autologous tumor-reactive T cells. There are several potential advantages with the use of adoptive cell transfer therapy in cancer treatment. Tumor specific T cells can be activated and expanded to large numbers ex vivo, independently of the immunogenic properties of the tumor, and functional and phenotypic qualities of T cells can be selected prior to their adoptive transfer.

After adoptive transfer, several events must occur for T cells to cause the regression of established tumors. More specifically:—T cells must be activated in vivo through antigen specific restimulation, —the T cells must then expand to levels capable of causing the destruction of significant tumor burdens, —antitumor cells must survive long enough to complete the eradication of all tumor cells.

Previously, the criterion used to selecting cells for adoptive transfer to patients with solid tumors was the ability of the antitumor T cells to release IFN-γ and kill tumor cells upon coculture. However, it is now clear that these criteria alone do not predict in vivo efficacy. Gattinoni et al., J. Clin. Invest. 115:1616-1626 (2005), found that CD $8^+$ T cells that acquire complete effector properties and exhibit increased antitumor reactivity in vitro are less effective at triggering tumor regressions and cures in vivo.

Methods according to prior art requires restimulation one or more times to reach clinically relevant levels of tumor specific cytotoxic T cells. See for example Ho et al. (Journal of Immunological Methods, 310 (2006), 40-50) and Gritzapis et al. (J. Immunol., 2008; 181; 146-154) wherein restimulation 1-2 times were necessary to reach a level of tumor specific CD8+ T cells of about 19%. Restimulation makes the cells less active and closer to apoptosis.

The transfer of genes into primary human lymphocytes permits the introduction of tumor antigen receptor molecules that can endow the engineered cell with antitumor specificity (Vera et al., Curr Gene Ther. 2009; 9:396-408.; Sadelain et al., Nat Rev Cancer. 2003; 3:35-45; Murphy et al., Immunity. 2005; 22:403-414.). Autologous peripheral blood lymphocytes (PBLs) can be modified to express a tumor antigen-reactive T-cell receptor (TCR). Yang et al., (J. Immunother., 2010, vol. 33; 648-658) discloses a method of generating antitumour T cells by in vitro transduction. They use a lentiviral mediated system to genetically modify CD8+ T cells to express antitumor T-cell antigen receptors (TCRs). In order to efficiently expand CD8+ T cells, a rapid expansion (REP) protocol (Ridell et al, U.S. Pat. No. 5,827,642; 1998), consisting of irradiated feeder cells from allogeneic peripheral blood mononuclear cells (PBMC) plus anti-CD3 antibody, was used. However, even if highly efficient in expansion of T cells in vitro, the REP protocol usually induces T cells with sub-optimal ability to survive and expand after reinfusion (Robbins et al, Journal of Immunology, 2004, 173:7125-30).

There is a therefore a great need for a method of preparing a T cell population for use in adoptive immunotherapy that increases proliferation and survival of antigen-specific T cells after reinfusion.

SUMMARY

The present invention relates to an in vitro method for priming of genetically modified antigen specific CD4+ and/or CD8+ T cells suitable for administration to a patient having a tumor. The method comprises co-culturing antigen receptor expressing target T cells from the patient to be treated, dendritic cells, anti-CD3 antibodies and lymphocytes that have been sensitized against MHC class I and/or MHC class II antigens on antigen presenting cells (APCs).

The present invention also relates to the antigen specific CD4+ and/or CD8+ T cells obtainable by the method and uses thereof.

DEFINITIONS

Figure 1:
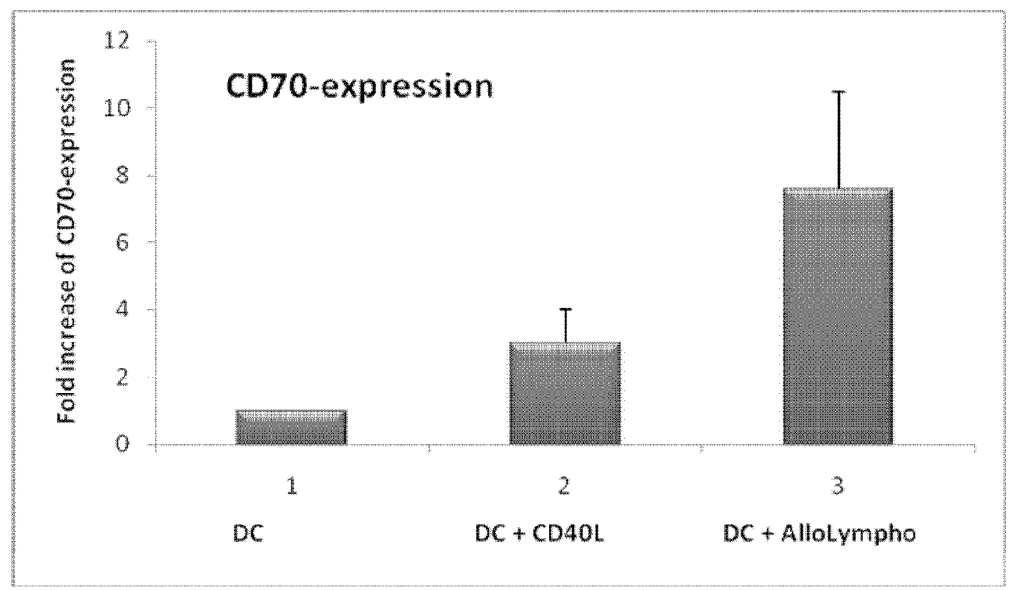
FIG. 1 illustrates that lymphocytes that have been sensitized against MHC antigens expressed on irradiated allogeneic peripheral blood mononuclear cells (PBMCs) in a conventional MLR (=allo-sensitized allogeneic lymphocytes; ASALs) markedly enhance the expression of CD70 on co-cultured mature monocyte-derived DCs which are autologous with respect to the irradiated PBMCs that were used for priming of ASALs.

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

Also, the term "about" is used to indicate a deviation of +/−2% of the given value, preferably +/−5%, and most preferably +/−10% of the numeric values, where applicable.

In the context of the present invention the term "antigen-specific" relates to the specific recognition/binding by a unique T cell receptor (TCR) of a short unique peptide sequence presented on a self MHC molecule.

In the context of the present invention the term "priming" and "activation" relates to a programmed activation process that occurs in a naive antigen-specific T cell that become stimulated by antigen-presenting cells with or without concurrent presence of "helper" cells.

In the context of the present invention the term "responder cells" relates to different lymphocyte subpopulations, including, but not limited to, T cells, NK cells and NKT cells which respond to co-cultured allogeneic PMBCs by activation and/or proliferation.

In the context of the present invention the term "sensitized cells" relates to different lymphocyte subpopulations, including T cells, NK cells and NKT cells which have been pre-activated by co-cultured allogeneic cells, including PBMCs.

In the context of the present invention the term "target cells" relates to $CD4^+$ or $CD8^+$ T cells that become stimulated by either allogeneic or autologous APCs in combination with antibodies, such as anti-CD3 antibodies. Sites of patient lymphocyte (target cell) collection can, for example, be peripheral blood, tumor, tumor-draining lymph node or bone marrow.

In the context of the present invention the term "mature" in relation to monocyte-derived DCs relates to their expression of "maturity-markers", including, but not limited to, CD40, CD86, CD83 and CCR7 that is induced by the stimulation of immature DCs with microbial products such as LPS or inflammatory mediators such as TNF-alpha and/or IL-1 beta.

Immature DCs are cells characterized by high endocytic activity and low T-cell activation potential. Immature DCs constantly sample the surrounding environment for pathogens such as viruses and bacteria. Immature DCs phagocytose pathogens and degrade their proteins into small pieces and upon maturation present those fragments at their cell surface using MHC molecules. Simultaneously, they upregulate cell-surface receptors that act as co-receptors in T-cell activation such as CD80, CD86, and CD40 greatly enhancing their ability to activate T-cells. They also upregulate CCR7, a chemotactic receptor that induces the dendritic cell to travel through the blood stream to the spleen or through the lymphatic system to a lymph node. Here they act as antigen-presenting cells: they activate helper T-cells and killer T-cells as well as B-cells by presenting them with antigens derived from the pathogen, alongside non-antigen specific costimulatory signals. Mature DCs probably arise from monocytes, white blood cells which circulate in the body and, depending on the right signal, can turn into either DCs or macrophages. The monocytes in turn are formed from stem cells in the bone marrow. Monocyte-derived DCs can be generated in vitro from peripheral blood monocytes.

In the context of the present invention the term "non-proliferative" of a cell is used to indicate that the cell has been rendered incapable of cell division to form progeny. The cell may nonetheless be capable of response to stimulus, or biosynthesis and/or secretion of cell products such as cytokines. Methods of making cells non-proliferative are known in the art. Preferred methods of making cells non-proliferative are treatment with anti-proliferative drugs such as mitomycin C, or irradiation, such as gamma irradiation. Cells that have been fixed or permeabilized and are incapable of division are also examples of non-proliferative cells.

In the context of the present invention the term "mixed lymphocyte reaction", mixed lymphocyte culture", "MLR", and MLC are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes. A frequent objective of an MLR is to provide allogeneic stimulation such as may initiate proliferation of the lymphocytes; but unless indicated, proliferation during the culture is not required. In the proper context, these terms may alternatively refer to a mixture of cells derived from such a culture.

As used herein, the term "treatment" refers to clinical intervention in an attempt to alter the natural course of the individual or cell being treated, and may be performed either for prophylaxis or during the course of clinical pathology. Desirable effects include preventing occurrence or recurrence of disease, alleviation of symptoms, and diminishment of any direct or indirect pathological consequences of the disease, preventing metastasis, lowering the rate of disease progression, amelioration or palliation of the disease state, and remission or improved prognosis.

The terms "antigen-presenting cell(s)", "APC" or "APCs" include both intact, whole cells as well as other molecules (all of allogeneic origin) which are capable of inducing the presentation of one or more antigens, preferably in association with class I MHC molecules, and all types of mononuclear cells which are capable of inducing an allogeneic immune response. Preferably whole viable cells are used as APCs. Examples of suitable APCs are, but not limited to, whole cells such as monocytes, macrophages, DCs, monocyte-derived DCs, macrophage-derived DCs, B cells and myeloid leukemia cells e. g. cell lines THP-1, U937, HL-60 or CEM-CM3. Myeloid leukemia cells are said to provide so called pre-monocytes.

The terms "cancer", "neoplasm" and "tumor" are used interchangeably and in either the singular or plural form, as appearing in the present specification and claims, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e. g. by such procedures as CAT scan, magnetic resonance imaging (MRI), X-ray, ultrasound or palpation. Non-limiting examples of tumors/cancers relevant for the present invention are carcinomas (e.g. breast cancer, prostate cancer, lung cancer, colorectal cancer, renal cancer, gastric cancer and pancreatic cancer), sarcomas (e.g. bone cancer and synovial cancer), neuro-endocrine tumors (e.g. glioblastoma, medulloblastoma and neuroblastoma), leukemias, lymphomas and squamos cell cancer (e.g. cervical cancer, vaginal cancer and oral cancer). Further, non-limiting examples of tumors/cancers relevant for the present invention are, glioma, fibroblastoma, neurosarcoma, uterine cancer, melanoma, testicular tumors, astrocytoma, ectopic hormone-producing tumor, ovarian cancer, bladder cancer, Wilm's tumor, vasoactive intestinal peptide secreting tumors, head and neck squamous cell cancer, esophageal cancer, or metastatic cancer. Prostate cancer and breast cancer are particularly preferred.

In the context of the present invention the term "culturing" refers to the in vitro propagation of cells or organisms in media of various kinds. It is understood that the descendants of a cell grown in culture may not be completely identical (morphologically, genetically, or phenotypically) to the parent cell. A suitable culturing medium can be selected by the person skilled in the art and examples of such media are RPMI medium or Eagles Minimal Essential Medium (EMEM).

The terms "major histocompatibility complex" and "MHC" refer to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of a chain encoded in the MHC associated non-covalently with β2-microglobulin. Class I MHC molecules are expressed by nearly all nucleated cells and have been shown to function in antigen presentation to CD8+ T cells. Class I molecules include HLA-A, -B, and -C in humans. Class I molecules generally bind peptides 8-10 amino acids in length. Class II MHC molecules also include membrane heterodimeric proteins.

Class II MHCs are known to participate in antigen presentation to CD4+ T cells and, in humans, include HLA-DP, -DQ, and DR. Class II molecules generally bind peptides 12-20 amino acid residues in length. The term "MHC restriction" refers to a characteristic of T cells that permits them to recognize antigen only after it is processed and the resulting antigenic peptides are displayed in association with either a self class I or self class II MHC molecule.

The terms "vaccine", "immunogen", or immunogenic composition" are used herein to refer to a compound or composition that is capable of conferring a degree of specific immunity when administered to a human or animal subject. As used in this disclosure, a "cellular vaccine" or "cellular immunogen" refers to a composition comprising at least one cell population, which is optionally inactivated, as an active ingredient. The immunogens, and immunogenic compositions of this invention are active, which mean that they are capable of stimulating a specific immunological response (such as an anti-tumor antigen or anti-cancer cell response) mediated at least in part by the immune system of the host. The immunological response may comprise antibodies, immunoreactive cells (such as helper/inducer or cytotoxic cells), or any combination thereof, and is preferably directed towards an antigen that is present on a tumor towards which the treatment is directed. The response may be elicited or restimulated in a subject by administration of either single or multiple doses.

A compound or composition is "immunogenic" if it is capable of either: a) generating an immune response against an antigen (such as a tumor antigen) in a naive individual; or b) reconstituting, boosting, or maintaining an immune response in an individual beyond what would occur if the compound or composition was not administered. A composition is immunogenic if it is capable of attaining either of these criteria when administered in single or multiple doses.

Description

The present invention relates to the production of allo-sensitized allogeneic lymphocytes (ASALs) to promote increased proliferation and survival of antigen-specific T cells during their activation by antigen-presenting cells, including dendritic cells (DCs) in combination with anti-CD3 antibodies.

The present invention is based on in vitro studies using peripheral blood mononuclear cells (PBMCs), and subpopulations thereof, from human healthy blood donors where a positive regulatory role for ASALs in the induction of antigen-specific human $CD8^+$ T cell responses was demonstrated. Using an allogeneic in vitro model, tracking proliferation and survival of alloreactive $CD8^+$ T cells in the presence of ASALs, the proliferative capacity after re-stimulation was increased more that 5-fold and apoptotic cell death reduced from 10 to 5%.

Antigen-specific human $CD4^+$ and $CD8^+$ T cells can be generated in vitro through transduction or transfection of genes encoding tumor antigen receptors. The present invention relates to a method of preparing a T cell population for use in adoptive immunotherapy comprising T cells engineered (by viral transduction, transfection, electroporation or other methods of introducing genetic material) to express a T cell receptor (TCR) or a chimeric antigen-receptor (CAR) that recognize the target antigen; activating these engineered T cells with DCs in the presence of sensitized allogeneic lymphocytes and anti-CD3 antibodies; expanding these cells in culture; and reintroducing these cells back into the patient.

Addition of ASALs leads to a strongly up regulated expression of the co-stimulatory molecule CD70 on antigen-presenting DCs and to production of IL-12 and IFN-gamma, two factors with a well-known positive impact on T cell commitment into type 1 CD4+ and CD8+ T cells. Further, addition of ASALs also led to production of IL-2, a well-known growth factor for T cells. Notably, CD70-mediated interactions have recently been shown to promote survival of activated T cells throughout successive rounds of division and thereby contribute to the accumulation of effector T cells.

More specifically, the present invention relates to an in vitro method for priming of genetically modified antigen specific CD4+ and/or CD8+ T cells suitable for administration to a patient having a tumor. The method comprises co-culturing tumor antigen receptor expressing target T cells from the patient to be treated with DCs, anti-CD3 antibodies and lymphocytes sensitized against MHC class I and/or MHC class II antigens on antigen presenting cells (APCs), wherein the APCs preferably being allogeneic with respect to the lymphocytes and the dendritic cells preferably monocyte derived. The addition of anti-CD3 antibodies will lead to their binding to the dendritic cells by Fc/Fc-receptor interactions that enable the antibody-armed dendritic cells to directly interact and activate CD3-expressing T cells.

Target T cells can be transformed with T cell receptor (TCR) coding genes or alternatively through the use of a chimeric antigen receptor (CAR) that is capable of relaying excitatory signals to T cells in a non-MHC-restricted manner. These hybrid proteins, composed of an extracellular antigen recognition domain fused to an intracellular T-cell activation domain, may therefore be used in patients regardless of their human leukocyte antigen genotype. Prior to genetic transformation, the target T cells are preferably pre-stimulated with anti-CD3 antibodies in order to optimize subsequent transformation. Any suitable CAR can be used in the present invention. The CAR ligand should be expressed by the tumor cell. Selecting and preparing a suitable CAR is within the skills of the person skilled in the art. Non-limiting examples CAR ligands are VEGFR-2 (vascular endothelial growth factor receptor-2), Her2/neu, CEA (carcino embryonic antigen), CD19, CD20 and GD2 (ganglioside antigen).

Genetic transformation of TCR- or CAR-coding genes into T cells can be performed by using any suitable method known to the skilled person, such as transfection or transduction (see for example Sambrook et al., Molecular Cloning, A Laboratory Manual, 3rd ed., vol. 1-3, Cold. Spring Harbor Laboratory, Cold Spring Harbor, N.Y.). Transfection can be made using viral vectors. Non-limiting examples of viral vectors include retro, lenti, adeno, adeno-associated viral vectors. Transduction includes but is not limited to electrotransfer of plasmids, transposon/transposase systems and micro-injection The ASALs are responder cells obtained from a mixed leukocyte reaction and are subsequently cultured together with dendritic cells and target cells in a culture medium containing anti-CD3 antibodies. The ASALs can be autologous or allogeneic with respect to the patient and with respect to the dendritic cells. The dendritic cells can be autologous or allogeneic with respect to the patient to be treated and with respect to the stimulator cells used for primary MLR-induced activation of ASALs. The ASALs are selected from the group consisting of peripheral blood lymphocytes, including $CD4^+$ T cells, $CD8^+$ T cells and natural killer (NK) cells. The target cells are $CD4^+$ and/or $CD8^+$ T cells.

In the inventive method the CD3 antibodies will act as unspecific stimulator of the transfected T cells (the T cells will become activated when the anti-CD3 antibody binds to the CD3 molecule on the T cell. The transfected T cells and the dendritic cells are autologous or allogeneic. The CD3 antibodies will also restimulate the ASALs meaning that the ASALs can be autologous or allogeneic with respect to the dendritic cells. Preferably, the dendritic cells and the ASALs are allogeneic. The dendritic cells and the ASALs are also preferably, but not necessarily, allogeneic (i.e. from healthy blood donors) with respect to the transfected patient T cells Addition of ASALs further leads to an enrichment of a population of target $CD8^+$ T cells expressing high levels of CD27. $CD27^+$ $CD8^+$ T cells represent potentially more effective CTLs (cytotoxic T cells) for adoptive immunotherapy since they can provide an antigen-driven autocrine signal for proliferation. Such helper-independent CD8+ T cells would not require exogenous help in the form of IL-2 or $CD4^+$ T cells to survive and expand. Thus, the present invention provides methods for treating an immune-mediated disease by providing a subject with a $CD8^+$ T cell population that is programmed for strong cytotoxic activity in the absence or reduced presence of additional cytokines, such as IL-2, or $CD4^+$ T cells. The methods are particularly useful for ex vivo expansion of cytolytic, antigen-specific CD8+ T cells, but may also be used for expansion of tumor-specific $CD4^+$ T cells.

The percentage of cytolytic antigen-specific CD8+ T cells expressed as percentage of the total number of CD8+ T lymphocytes is preferably at least about 5%, more preferably at least about 10%, more preferably at least about 15%, more preferably at least about 20%, even more preferably at least about 25%, even more preferably at least about 30% and most preferably at least about 35%.

Both CD8+ and CD4+ T cells are needed for efficient cytotoxicity. The CD8+ T cells are cytotoxic while the CD4+ T cells release growth proliferating factors, such as IL-2. Preferably the number CD8+ T cells exceeds the number of CD4+ T cells since expansion protocols that favor expansion of CD4+ T cells over CD8+ T cells are expected to compromise in vivo anti-tumor efficacy (Yang et al. Journal of Immunotherapy 2010; 33:648.

More specifically, the method of the present invention relates to an in vitro method for priming of TCR- or CAR-transformed antigen specific CD4+ and/or CD8+ T cells suitable for administration to a patient having a tumor, said method comprising the following steps:

a) culturing non-proliferating antigen presenting cells from the patient or from a healthy donor together with peripheral blood mononuclear cells that are allogeneic with respect to the antigen presenting cells, b) culturing monocytes, from the patient or from a healthy donor, in a composition allowing the monocytes to mature to mature DCs. (the composition is further described below), and c) culturing allo-sensitized lymphocytes, including but not limited to $CD4^+$ T cells, $CD8^+$ T cells and/or natural killer (NK) cells from step a) with mature DCs from step b) together with TCR- or CAR-transformed target cells, including CD4+ T cells and CD8+ T cells, in a culture medium containing anti-CD3 antibodies.

Monocyte-derived DCs are obtained by first culturing monocytes in a composition comprising GM-CSF and IL-4 for about 2-7 days, preferably about 5 days to obtain immature DCs and subsequently add a second composition that enables the immature DCs to become mature DCs by culturing for at least about 12 to 72 hours and preferably about 24-48 hours. The second composition comprises components that allow the immature DCs to become mature monocyte-derived DCs that can be used to activate CD4+ and CD8+ T cells. In one embodiment the second composition comprises TNF alfa, IL-1 beta, interferon gamma, interferon beta and a TLR3 ligand, such as poly-I:C (Mailliard et al., Alpha-type-1 polarized DCs: a novel immunization tool with optimized CTL-inducing activity. Cancer Res. 2004; 64:5934-5937.). In another embodiment the second composition comprises interferon gamma, a TLR 3 and/or a TLR 4 ligand and a TLR7 and/or a TLR 8 ligand and/or a TLR9 ligand. Non-limiting examples of a TLR 3 ligand is poly-I:C, of a TLR7/8 ligand is R848, and of a TLR9 ligand is CpG.

The sensitization of allogeneic lymphocytes is induced by a traditional mixed leukocyte reaction (MLR or MLC—mixed leukocyte culture) comprising culturing inactivated antigen presenting cells with peripheral blood mononuclear cells (PBMCs) from a healthy donor, wherein the antigen presenting cells are allogeneic with respect to the lymphocytes. The performance of an MLR is well known to the skilled person (Jordan W J, Ritter M A. Optimal analysis of composite cytokine responses during alloreactivity. *J Immunol Methods* 2002; 260: 1-14. In an MLR PBMCs (mainly lymphocytes) from two individuals are mixed together in tissue culture for several days. Lymphocytes from incompatible individuals will stimulate each other to proliferate significantly (measured for example by tritiated thymidine uptake) whereas those from compatible individuals will not. In a one-way MLC, the lymphocytes from one of the individuals are pre-treated with anti-proliferative drugs such as mitomycin or with irradiation, thereby allowing only the untreated lymphocytes from the other individual to proliferate in response to foreign histocompatibility antigens.

The antigen presenting cells used in the MLR are selected from the group consisting of PBMCs and monocytes-derived DCs.

In the method of the present invention the cells (tumor antigen receptor expressing target T cells from the patient to be treated, dendritic cells, anti-CD3 antibodies and lymphocytes that have been sensitized against MHC class I and/or MHC class II antigens on antigen presenting cells (APCs)) are co-cultured for about 20 days, preferably for about 4 to 20 days, preferably 6 to 20 days, more preferably 7 to 14 days and most preferably about 9 to 14 days.

Exogenous IL-2, IL-7, IL-15, anti-IL-4 and/or IL-21 can be added to the cell culture in order to optimize cell proliferation and survival.

It is also possible to restimulate the primed antigen specific CD4+ and/or CD8+ T cells by culturing said cells together with new DCs, anti-CD3 antibodies and new sensitized lymphocytes that have been activated by non-proliferating antigen presenting cells that are allogeneic with respect to the lymphocytes, and optionally addition of exogenous IL-2, IL-7, IL-15, anti-IL-4 and/or IL-21 to the cell culture.

The present invention also relates to an immunogenic composition obtainable by the method described above as well as the antigen specific CD4+ and/or CD8+ T cells obtainable by the method described above.

The antigen specific CD4+ and/or CD8+ T cells are suitable for administration to a patient and preferably have at least one of the following features:
  ability to proliferate
  express low levels of the apoptosis marker Annexin-V (i.e. no more than 40%, preferably no more than 20%, of the cells should exhibit positive staining for Annexin-V by FACS determination)
  express CD27 and/or CD28 at their cell surface A further ability of the specific CD4+ and/or CD8+ T cells obtainable by the method of the invention is the ability to be activated by, and/or kill tumor cells or tumor-loaded antigen-presenting cells that are MHC-compatible with respect to the antigen specific T cells in vitro. The specific CD4+ and/or CD8+ T cells obtainable by the method of the invention also possess the ability to kill relevant tumor target cells in vitro despite preculture with immunosuppressive factors such as IL-10, TGF-beta and/or $H_2O_2$, have the ability to proliferate after killing of relevant tumor target cells in vitro as well as ability to proliferate after killing of relevant tumor target cells in vitro despite preculture with immunosuppressive factors such as IL-10, TGF-beta and/or $H_2O_2$.

The present invention relates to the antigen specific CD4+ and/or CD8+ T cells obtained by the inventive method for use as a medicament and for use of said the antigen specific CD4+ and/or CD8+ T cells for the manufacture of a medicament.

Further, the present invention relates to the use of antigen specific CD4+ and/or CD8+ T cells obtainable by the method of the invention or as defined above for use in the treatment of a tumor or for eliciting an anti-tumor immunological response in a human as well as for the manufacture of a medicament for the treatment of a tumor or for eliciting an anti-tumor immunological response in a human. The CD4+ and/or CD8+ T cells can be administered after the first stimulation or alternatively after restimulation. In one embodiment the CD4+ and/or CD8+ T cells are administered in combination with a therapeutic cancer vaccine.

Methods of using T cell populations for adoptive cell therapy in treatment of human subjects are known to clinicians skilled in the art. T cell populations prepared according to the methods described herein and known in the art can be used in such methods. For example, adoptive cell therapy using tumor-infiltrating lymphocytes, with MART-I antigen specific T cells have been tested in the clinic (Powell et al., Blood 105:241-250, 2005). Patients with renal cell carcinoma have been vaccinated with irradiated autologous tumor cells. Harvested cells were secondarily activated with anti-CD3 monoclonal antibody and IL-2 and then re-administered to the patients (Chang et al., J. Clinical Oncology 21:884-890, 2003.)

Antigen-primed T cells undergo increased proliferation and decreased apoptosis upon re-stimulation when exposed to ASALs during their initial DC-mediated priming in vitro. Thus, methods for enhancing secondary T cell responses upon vaccination if adoptively transferred back to the patient before and/or during vaccination are also contemplated by the present invention.

The present invention also provides methods for improving cancer vaccine therapy. Many tumors express foreign antigens that can potentially serve as targets for destruction by the immune system. Cancer vaccines generate a systemic tumor-specific immune response in a subject that comprises both humoral and cellular components. The response is elicited from the subject's own immune system by administering a vaccine composition at a site distant from the tumor or at the site of a localized tumor. The antibodies or immune cells bind the tumor antigen and lyse the tumor cells. However, there remains a need for increased T cell-responsiveness upon vaccination of cancer patients. Adoptive transfer of preactivated apoptosis-resistant tumor-specific T cells with high proliferative potential before, or at the time of vaccination, may therefore enhance vaccine-mediated immune responses in vivo.

The composition according to the invention can also be administered in combination with a therapeutic cancer vaccine. Non-limiting examples of such therapeutic cancer vaccines are ex vivo-propagated and tumor-loaded DCs, cytokine producing tumor cells, DNA-vaccination and vaccines using TLR-ligands in combination with tumor antigens.

The cells obtainable by the method of the invention can be administered directly to an organism, such as a human, to increase proliferation and survival of antigen-specific T cells during their activation. Administration of these cells, often with pharmaceutically acceptable carriers, is by any of the routes normally used for introducing a cell into ultimate contact with a mammal's blood or tissue cells.

Formulations suitable for parenteral administration, such as, for example, by intravenous, intramuscular, intradermal, intraperitoneal, subcutaneous and intratumoral routes and carriers include aqueous isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Intravenous administration is the preferred method of administration for the CD4+ and/or CD8+ T cells of the invention.

The dose of the CD4+ and/or CD8+ T cells administered to a patient, in the context of the present invention should be sufficient to enhance the immune response in the patient. Thus, cells are administered to a patient in an amount sufficient to elicit an effective immune response to the tumor antigen and/or to alleviate, reduce, cure or at least partially arrest symptoms and/or complications from the disease. An amount adequate to accomplish this is defined as a "therapeutically effective dose". The dose will be determined by the activity of the cells produced and the condition of the patient, as well as the body weight or surface area of the patient to be treated. In determining the effective amount of the cell to be administered in the treatment or prophylaxis of diseases such as cancer the physician needs to evaluate progression of the disease and the induction of immune response against any relevant tumor antigens.

There are several major advantages of the invention compared to methods of the prior art. The present invention provides a high level of tumor specific CD8+ T cells without the need of restimulation. Restimulation makes the cells less active and brings them closer to apoptosis. Thus, a method that efficiently expands tumor specific T cells without the need for restimulation is an advantage. In addition, without the need to restimulate the cells, the tumor specific T cells can be brought back to the patient in a shorter period of time and it is more cost efficient. Further, with the use of the method according to the present invention there is no need for depletion of suppressor cells or the addition of exogenous growth factors which are very costly processes. Adoptive transfer of autologous tumor specific T cells that are cultured from tumor infiltrating lymphocytes can cause regressions of advanced tumors in humans but cannot be reliably cultured from most human tumors, Methods have therefore been developed to engineer a large number of blood-derived T cells to express genes encoding tumor-antigen-specific T cell receptors. In the case of a chimeric antigen receptor (CAR), it can be used in patients regardless of their human leukocyte antigen genotype.

Although the expansion efficacy of the inventive method is similar to the REP protocol, the ASALs expanded with the present method have a much higher killing ability in vivo compared to the REP expanded T cells. The main reason for this is that the REP produced T cells are less resistant to the immunosuppressive environment created by the tumor compared to the T cells expanded with the method according to the present invention. Further, the inventive method expands CD8+ T cells at a higher ratio compared to the REP protocol which is beneficial as protocols that favor CD4+ T cell expansion show reduced in vivo anti-tumor efficacy.

Encompassed by the present invention is any combination of the different aspects and features disclosed.

The invention is further illustrated by the following non-limiting examples.

EXAMPLES

Example 1

Material & Methods

Allosensitized allogeneic lymphocytes (ASALs) were generated in a standard one-way mixed leukocyte reaction (MLR) by co-culturing gamma irradiated PBMC from a healthy blood donor with non-irradiated PBMCs from an allogeneic donor (with respect to the healthy blood donor) at a ratio of 1:1 in serum-free X-VIVO 15 medium in tissue culture flasks for 5-7 days. For propagation of immature DCs, peripheral blood mononuclear cells (PBMCs) obtained from healthy blood donors were isolated on density gradients (Lymphoprep, Nycomed, Oslo, Norway). Isolated PBMCs were resuspended in AIM-V medium (Invitrogen, Paisley, UK), plated in 24-well plastic culture plates at $2.5 \times 10^6$ cells per well and allowed to adhere for 2 hours. Non-adherent cells were removed and the remaining adherent monocytes, were cultured in AIM-V medium supplemented with recombinant human GM-CSF and IL-4 (R&D Systems, Abingdon, UK; both at 1,000 U/mL) for 4-6 days. Maturation of immature DC was induced by supplementing the culture media with IFN-α (3,000 U/mL), IFN-γ (1,000 U/mL), TNF-α (50 ng/mL), IL-1β (25 ng/mL) (all from R&D Systems) and p-I:C (Sigma-Aldrich; 20 μg/mL) during the last 24 hours of incubation.

The mature DC populations all contained more than 70% CD83+ DCs as determined by FACS analysis.

After washing, mature DCs were co-cultured with non-irradiated or gamma-irradiated (25 Grey) ASALs in X-VIVO 15 medium for 24 h and analyzed by FACS. Sensitization of alloreactive lymphocytes was performed by conducting a primary one-way MLR in serum-free culture media (X-VIVO 15) for 5-6 days with gamma-irradiated PBMCs as stimulator cells and non-irradiated PBMCs as responder cells. PE-conjugated anti-human CD70 was used for FACS studies.

Results:

As shown in FIG. 1, ASALs markedly enhance the expression of CD70 on mature monocyte-derived DCs which are autologous with respect to the irradiated PBMCs used for priming of ASALs.

Figure 2:
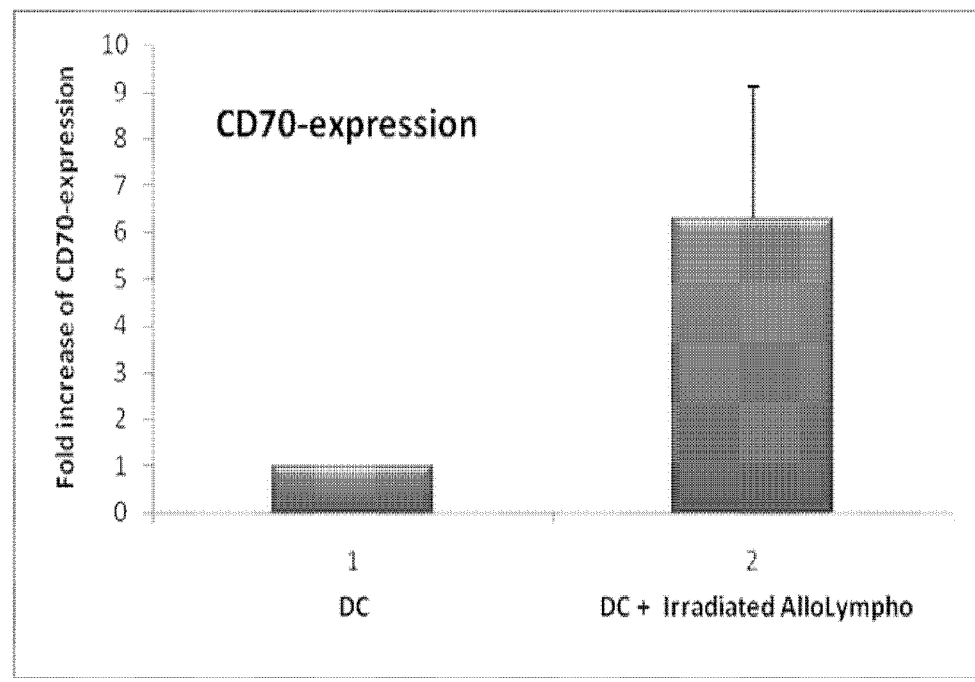
FIG. 2 illustrates that gamma-irradiated ASALs enhance the expression of CD70 on co-cultured mature monocyte-derived DCs which are autologous with respect to the irradiated PBMCs used for priming of ASALs.

As shown in FIG. 2, gamma-irradiated ASALs similarly enhance the expression of CD70 on mature monocyte-derived DCs which are autologous with respect to the irradiated PBMCs used for priming of ASALs.

Figure 3:
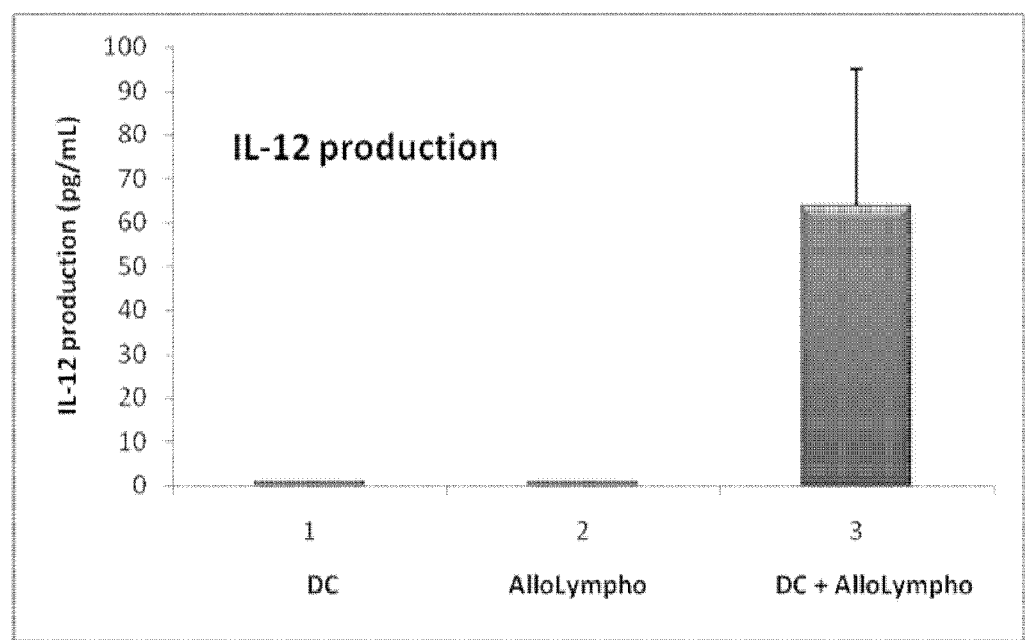
FIG. 3 illustrates that co-culture of ASALs with monocyte-derived DCs which are autologous with respect to the irradiated PBMCs used for priming of ASALs induce substantial IL-12 production.
Figure 4:
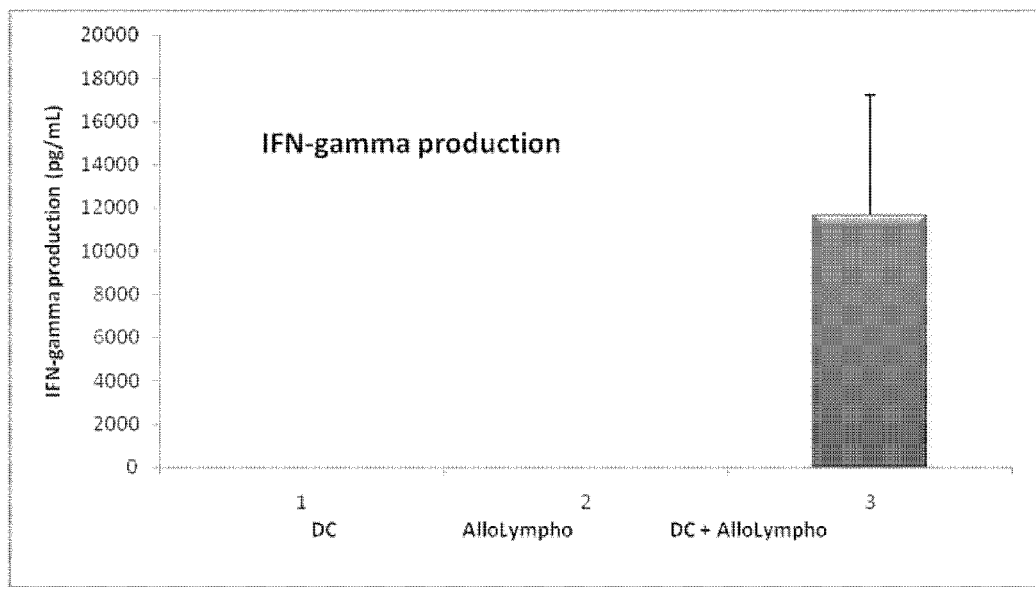
FIG. 4 illustrates that co-culture of ASALs with monocyte-derived DCs which are autologous with respect to the irradiated PBMCs used for priming of ASALs induce substantial IFN-gamma production.
Figure 5:
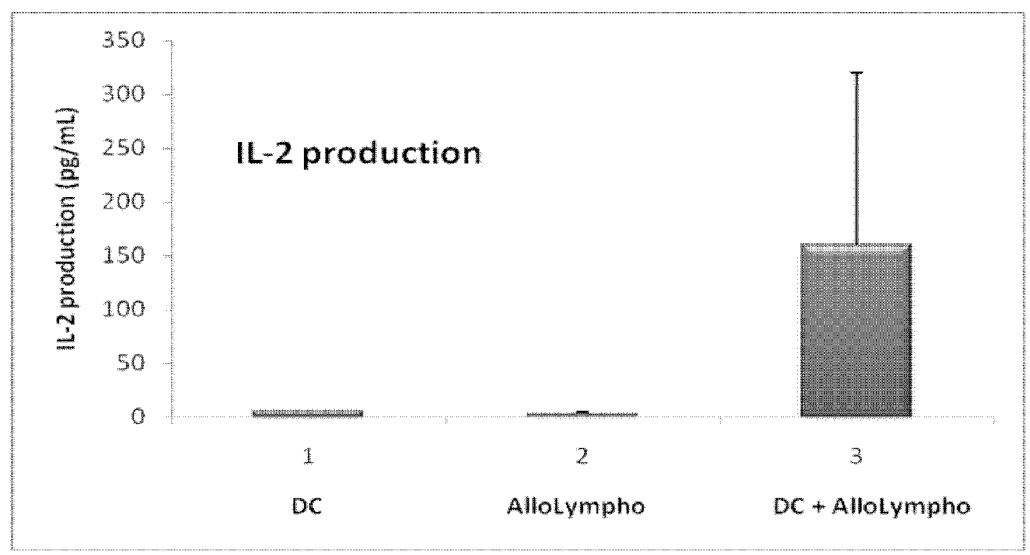
FIG. 5 illustrates that co-culture of ASALs with monocyte-derived DCs which are autologous with respect to the irradiated PBMCs used for priming of ASALs, induce substantial IL-2 production.

As shown in FIGS. 3, 4 and 5 co-culture of ASALs with mature DCs which are autologous with respect to the irradiated PBMCs used for priming of ASALs, induce a substantial production of IL-12, IFN-gamma and IL-2.

Example 2

Material and Methods

ASALs were generated during a conventional MLR for 7 days using irradiated allogeneic PBMCs as stimulators (see Example 1). After harvest and irradiation, the bulk population of ASALs ("MLR") or ASALs depleted of CD4+, CD8+ or CD56+ (NK/NKT) cells were co-cultured with mature allogeneic monocyte-derived DCs (autologous with respect to the PBMCs used for priming of ASALs). Co-culture supernatants were collected after 24 h and subsequently assayed for IL-2, IL-12 and IFN-gamma production.

Figure 6:
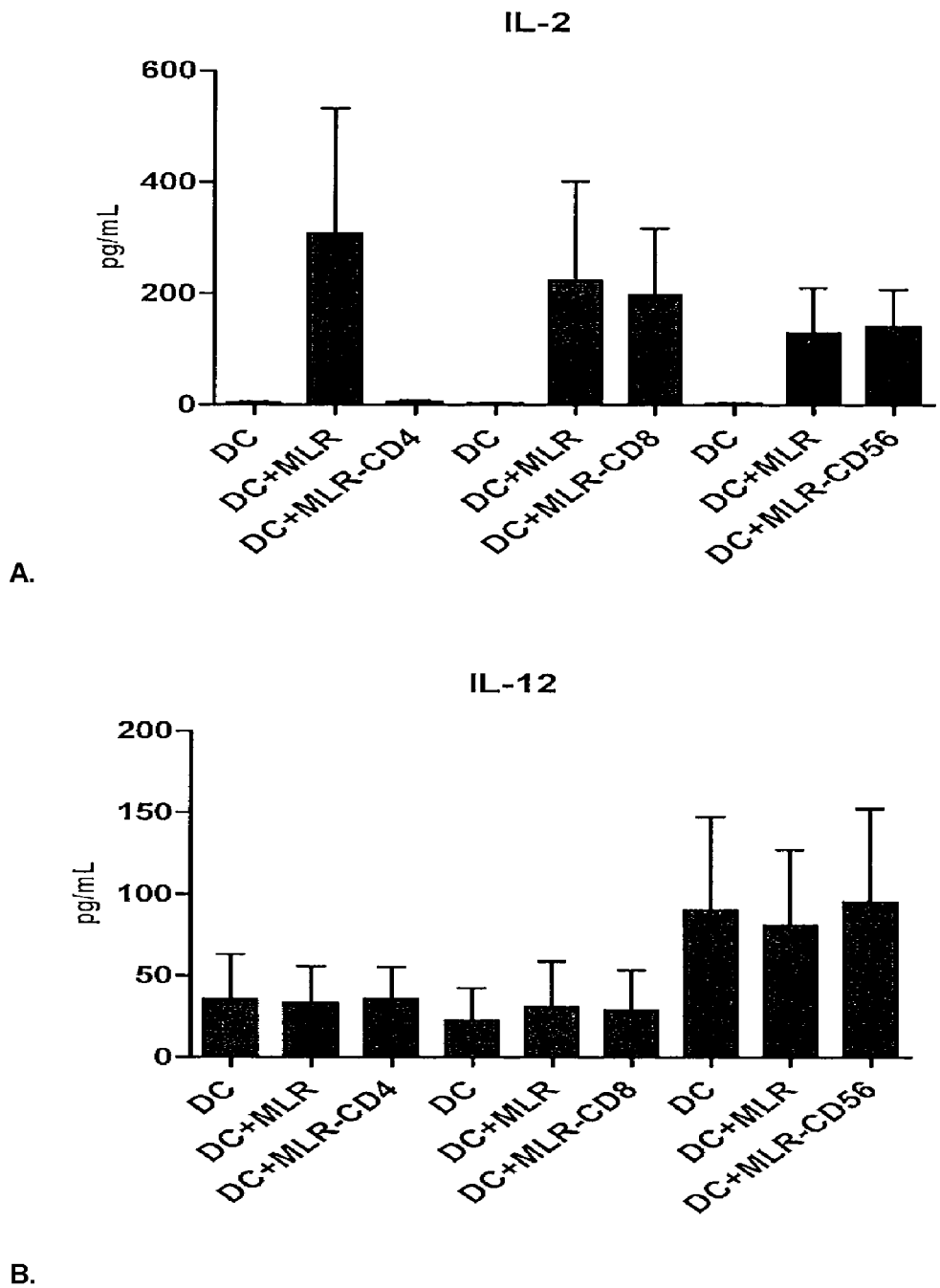
FIG. 6 illustrates the production of IL-2, IL-12 and IFN-gamma and as a result of co-culture of mature monocyte-derived DCs with ASALs that have been depleted of $CD4^+$, $CD8^+$ or $CD56^+$ lymphocytes.

Results:

IL-2 production was found to be strictly CD4-dependent (FIG. 6A), while IL-12 production (FIG. 6B) showed no ASAL-dependence at all and IFN-gamma production (FIG. 6C) showed partial dependence on co-cultured and alloprimed CD4+, CD8+ and CD56+ (NK/NKT) within the ASAL-population.

Example 3

Material and Methods

Immature DCs were generated by plastic adherence of monocytes. Monocytes were cultured for 7 days in Cell-Gro® DC supplemented with IL-4 and GM-CFS, both at 1000 U/mL. Maturation of DCs was induced by the addition of 50 ng/mL TNF-α, 25 ng/mL IL-1β, 50 ng/mL IFN-γ 3000 U/mL IFN-α and 20 µg/mL Poly I:C during the last 2 days of incubation.

ASALs were generated in a one-way mixed lymphocyte reaction by co-culturing gamma irradiated allogenic PBMC and non-irradiated autologous PBMC, with respect to DC donor, at a ratio of 1:1 in X-VIVO 15 for 7 days.

CD8+ T lymphocytes were isolated by positive selection from autologous PBMC which had been cultured in X-VIVO 15 supplemented with 50 ng/mL IL-15 at a final concentration of $0.5 \times 10^6$ lymphocytes/mL for 7 days. PBMC were centrifuged and re-suspended in PBS-0.5% BSA-2M EDTA at a final concentration of $1 \times 10^7 / 80$ µL. PBMC were incubated with CD8+ MicroBeads (Miltenyi Biotec) for 15 min at 4° C., washed, re-suspended and placed onto a LS MACS column. Unlabeled cells were washed through and total effluent containing CD8+ lymphocytes were collected. Isolated CD8+ T lymphocytes were resuspended in pre-warmed PBS-1% A BSA to a concentration of $1 \times 10^6$/mL and stained with 10 µM CFSE (Molecular probes Invitrogen) for 10 min at 37° C. Staining was terminated by addition of 5 mL ice-cold X-VIVO 15 medium and incubated on ice for 5 min. Cells were washed twice in medium and re-suspended to a final concentration of $1 \times 10^6$/mL. Stained CD8+ T lymphocytes were co-cultured for 4-7 days with irradiated allosensitized allogenic PBMC and matured autologous DC at a ratio of 4:4:1. Following culture, lymphocytes were harvested and stained with CD3-APC-H7, CD8-PerCP, CD27-APC and Annexin V. The percentage of proliferating CD8+ T lymphocytes was determined by flow cytometry and expressed as percentage of total lymphocytes.

Figure 7:
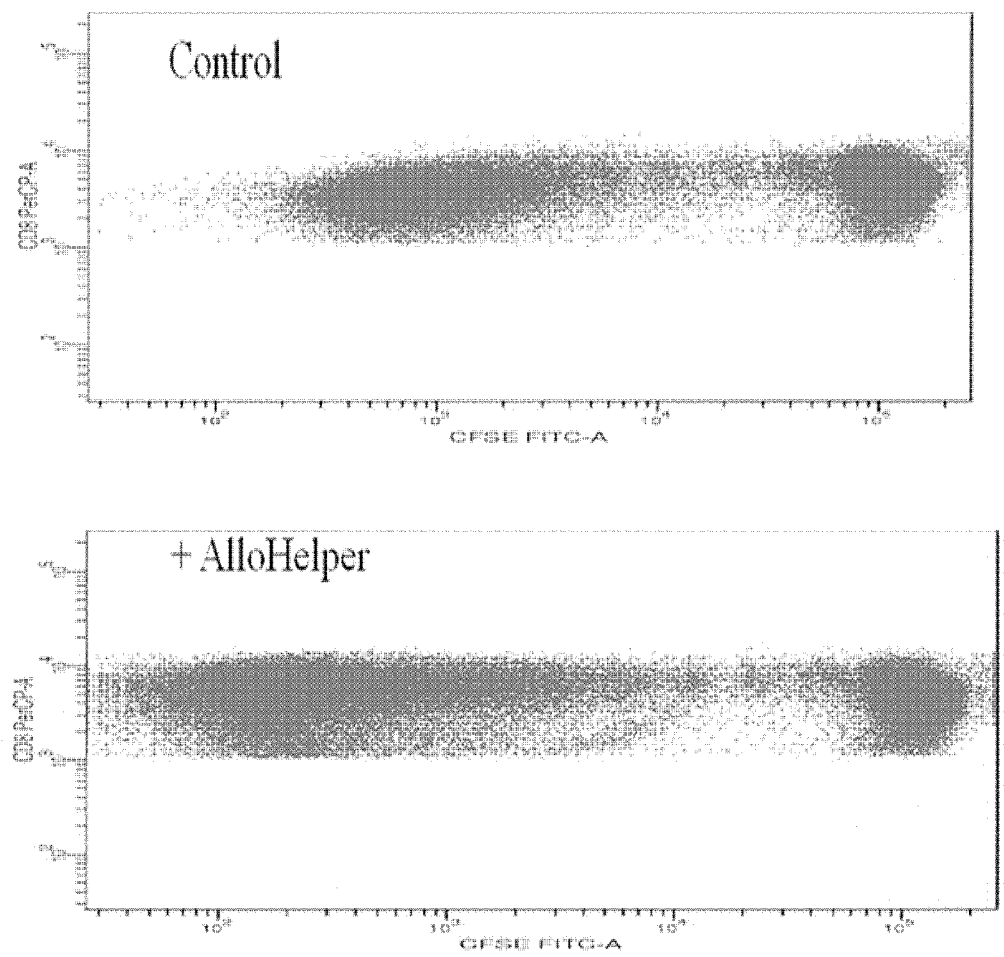
FIG. 7 illustrates that co-culture of ASALs with monocyte-derived DCs, which are autologous with respect to the irradiated PBMCs that were used for priming of ASALs, increase the proliferative response in non-sensitized allogeneic $CD8^+$ T cells.

Results:

Results: As illustrated in FIG. 7, addition of irradiated "AlloHelpers" (=ASALs) strongly increase CD8+ T cell divisions (more cells with low fluorescence intensity=more dots to the left in the dot-plot). ASALs thus augment the ability of monocyted-derived DCs to induce a proliferative response in alloreactive CD8+ T cells.

Example 4

Material and Methods

See M&M in example 1.

CD8+ lymphocytes were isolated (using negative selection with antibody-coated magnetic beads) after co-culture of DCs, irradiated ASALs (allogeneic to the DCs) for 6 days and subsequently restimulated with B-cells (autologous to the DCs used during primary stimulation) and stained for expression of CD27 and Annexin-V. Subsequent analysis was performed with FACS.

Figure 8:
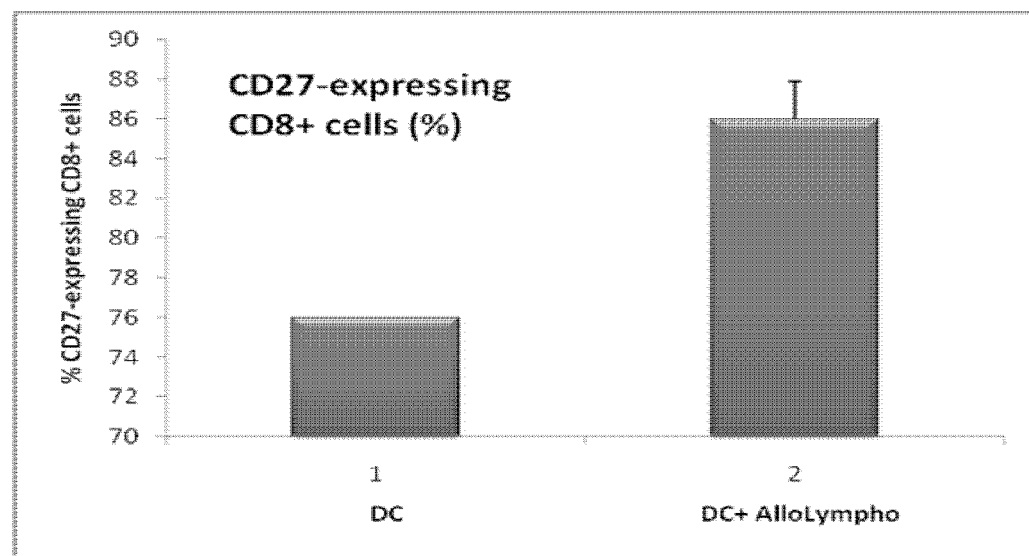
FIG. 8 illustrates that addition of irradiated ASALs to monocyte-derived DCs, which are autologous with respect to the irradiated PBMCs used for priming of ASALs, during primary stimulation of allogeneic $CD8^+$ target cells leads to increased numbers of CD27-expressing alloreactive $CD8^+$ target cells when these target cells are restimulated with B-cells that are autologous with respect to the DCs used for primary target cell stimulation.

Results:

As shown in FIG. 8, addition of ASALs during primary stimulation substantially increased expression of CD27 when the CD8+ cells were re-stimulated with B-cells.

Figure 9:
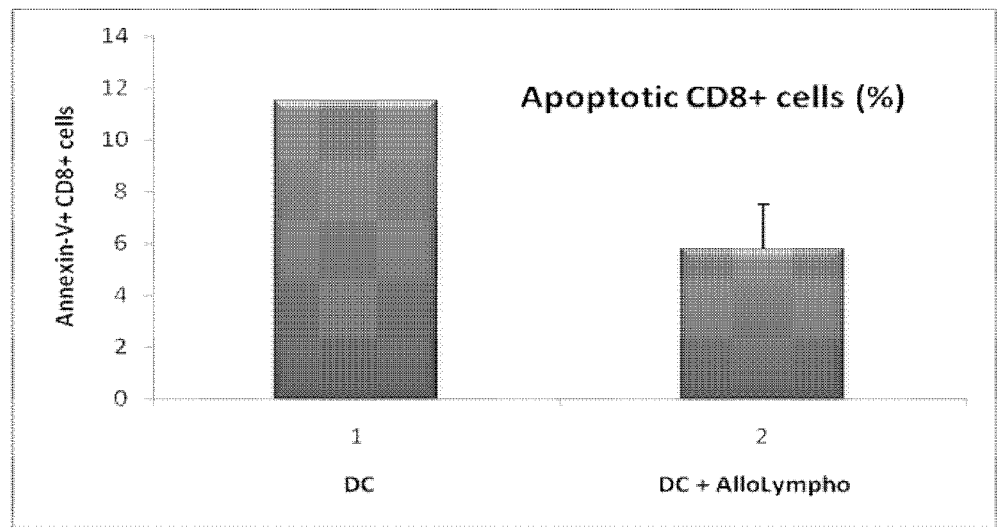
FIG. 9 illustrates that addition of irradiated ASALs to irradiated PBMCs, which are autologous with respect to the irradiated PBMCs used for priming of ASALs during primary stimulation of allogeneic $CD8^+$ target cells leads to decreased numbers of apoptotic (Annexin-V-positive) target cells when these target cells are restimulated with B-cells that are autologous with respect to the DCs used for primary target cell stimulation.

Addition of ASALs during primary stimulation substantially reduced expression of Annexin-V (apoptosis marker) when the CD8+ cells were re-stimulated with B-cells (see FIG. 9) thus making the CD8+ T cells more resistant to enter apoptosis.

Example 5

Material and Methods

See M&M in example 4.

Before restimulation with B-cells the primed and isolated CD8+ cells were pulsed with 3H-Thymidine.

Figure 10:
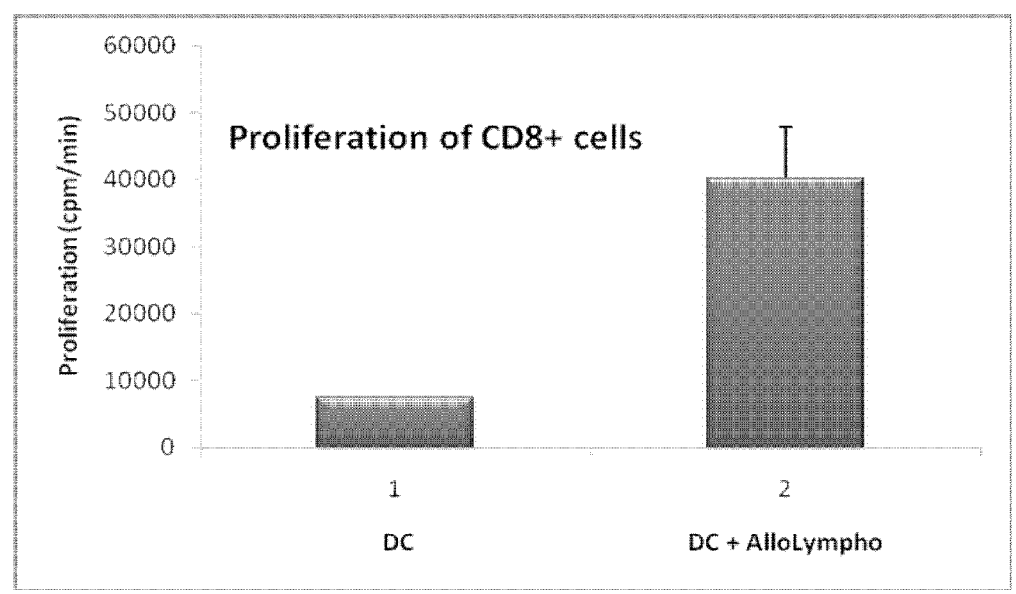
FIG. 10 illustrates that addition of irradiated ASALs to irradiated monocyte-derived DCs, which are autologous with to the irradiated PBMCs used for priming of ASALs, during primary stimulation of allogeneic $CD8^+$ target cells leads to a stronger (6-fold) secondary proliferative response when these alloreactive $CD8^+$ target cells are restimulated with B-cells that are autologous with respect to the DCs used for primary target cell stimulation.

Results:

As shown in FIG. 10, addition of ASALs during primary stimulation strongly increased the proliferative response (as measured by incorporation of 3H-Thymidine, cpm/min, day 3) of alloreactive CD8+ cells after restimulation.

Example 6

Material and Methods

See M&M in example 4.

After co-culture of B-cells and pre-activated CD8+ cells for 2 days culture supernatant was collected and analyzed for IFN-gamma production by a conventional ELISA (R&D Systems).

Figure 11:
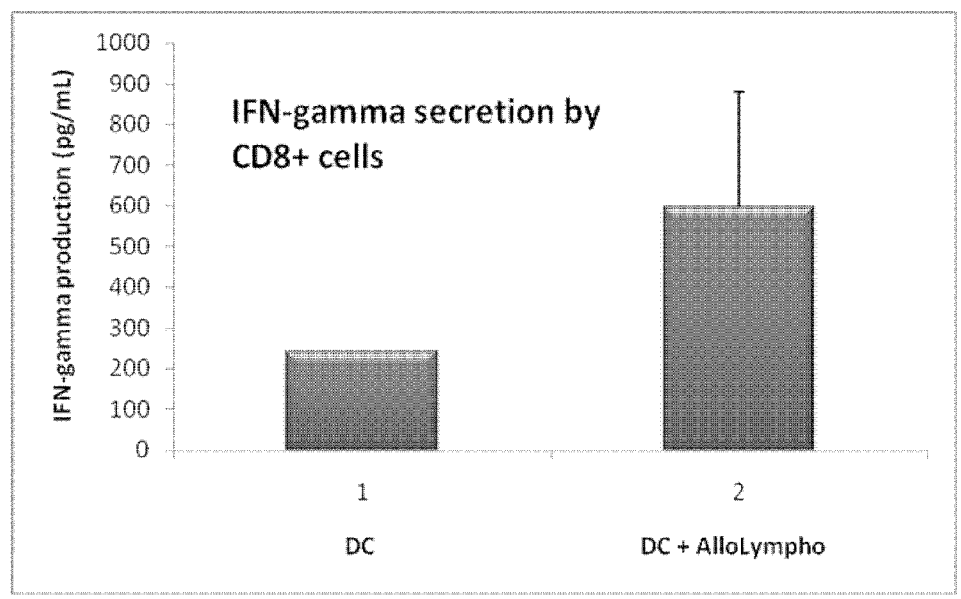
FIG. 11 illustrates that addition of irradiated ASALs to irradiated monocyte-derived DCs, which are autologous with respect to the irradiated PBMCs used for priming of ASALs, during primary stimulation of allogeneic $CD8^+$ target cells leads to a substantial increase of IFN-gamma production when these alloreactive $CD8^+$ target cells are restimulated with B-cells that are autologous with respect to the DCs used for primary target cell stimulation.

Results:

FIG. 11 shows that addition of ASALs during primary stimulation substantially increased production of IFN-gamma by alloreactive CD8+ cells after restimulation.

Example 7

Expansion of CAR-Transfected T Cells

Material and Methods:

The basal culture medium consisted of RPMI Media 1640 supplemented with 10% human serum, 1% penicillin (100 U/ml), 1% HEPES, 0.5% L-glutamine and 160 µl β mercapto-ethanol.

Immature DCs were generated by plastic adherence of monocytes. Monocytes were subsequently cultured for 7 days in basal culture medium supplemented with IL-4 and GM-CFS, both at 1000 U/mL. Maturation of DCs was induced by the addition of 20 ug/mL Poly-I:C, 2.5 ug/mL R848 and 50 ng/mL IFN-gamma during the last 24 hours of incubation.

ASALs were generated in a one-way mixed lymphocyte reaction by co-culturing gamma irradiated PBMC and non-irradiated allogeneic PBMC at a ratio of 1:1 in basal culture medium for 7 days.

T cell transfection: Isolated PBMCs ($5 \times 10(5)$/mL) were initially activated for 3 days by adding IL-2 (100 IU/mL) and anti-CD3 (OKT3) (50 ng/mL) to the DC media. Thereafter the non-adherent cells (mainly activated T cells) were transfected with CAR against GD2 (a ganglioside antigen which is highly expressed on neruoblastoma cells), by incubation in culture medium containing CAR-lentivirus (20 uL), Sequa-Brene (1 mg/mL) and IL-2 (100 IU/mL) during 4 hours. After washing the cells were cultured in medium supplied with IL-2 (100 IU/mL) for 5 days. Transfection level was thereafter analyzed by flow cytometry using PE-A conjugated antibodies against lentiviral-CAR.

T cell expansion: After washing, the CAR-transfected T cells were subsequently expanded in culture medium for 12 days in T-25 flasks using either the ASAL protocol consisting of mature DCs+irradiated ASALs+CAR-transfected T cells (1:4:1 ratio), IL-2 (100 IU/mL) and OKT3 (50 ng/mL) or the standard REP protocol (Yang et al, Journal of Immunotherapy 2010; 33:648) consisting of irradiated allogeneic PBMCs from 3 different donors+CAR-transfected T cells (100:1 ratio), IL-2 (100 IU/mL) and OKT3 (50 ng/mL). At day 3, 6 and 9, the culture medium was removed and replenished with fresh medium, 100 IU/mL IL-2 and 50 ng/mL OKT3 for extended culture.

Flow cytometry analysis: The cells were washed with PBS twice and stained for 15 min at room temperature (avoiding light) by using specific fluorophore (fluorescein isothiocyanate (FITC), APC, or phycoerythrin (PE))-labeled antibodies (BD Biosciences, SanDiego, Calif.) against cell surface markers (CD3, CD4, CD8, CD27 CD64 and CAR (GD2)). The FACS analysis was performed on BD FACS Canto II (BD Biosciences, USA) and the data were analyzed with BD FACS Canto II software.

Apoptosis assay: The Annexin V apoptotic assay (BD Biosciences) was used to evaluate the viability of T cells after expansion for 12 days with different expansion protocols in control medium and in medium where apoptosis-inducing agents (H2O2 or doxorubicin) were subsequently added for 24 hours. Briefly, T cells were washed with PBS twice and re-suspended in binding buffer and then incubated with Annexin V-fluorescein isothiocyanate (FITC) and propidium iodide (PI) for 15 min at room temperature, followed by wash and flow cytometry analysis Measurement of Tumor Cell Killing:

CAR-transfected and expanded (12 days) T cells were co-cultured for 48 hours with the GD2-expressing neuroblastoma cell line IMR-3 (co-expressing the Luciferase report gene) at different effector:target cell ratios (E:T ratio) in each well of a round-bottom 96-well plate. The ability of transfected and expanded T cells to lyse relevant tumor cells was evaluated using a luciferase expression assay (Fu et al, PloS 1, 2010, 5,e11867). The relative cell viability (%) was calculated as raw light unit (RLU) and normalized to the luciferase activity from target cells (IMR-3) without effector T cells.

Tumor cell killing by T cells exposed to potential tumor-derived suppressive factors was also estimated by flow cytometry using conjugated antibodies against membrane bound CD107a which is a marker of lytic granule exocytosis on effector T cells. T cells were exposed with IL-10 (10 ng/mL) and TGF-beta (2.5 ng/m L) for 4 hours, H2O2 (25 uM) for 24 hours or IL-10 and TGF-beta (both for 4 hours) in combination with H2O2 (24 hours) before co-culture with target cells.

The CellTrace™ CFSE cell proliferation kit (Invitrogen, Eugene, Oreg., USA) was used to evaluate T-cell proliferation 4 days after interaction/killing of target antigen-expressing tumor cells with or without prior exposure to potential tumor-derived suppressive factors. T cells were exposed with IL-10 (10 ng/mL) and TGF-beta (2.5 ng/mL) for 4 hours, H2O2 (25 uM) for 24 hours or IL-10 and TGF-beta (both for 4 hours) in combination with H2O2 (24 hours) before co-culture with target cells.

Figure 12:
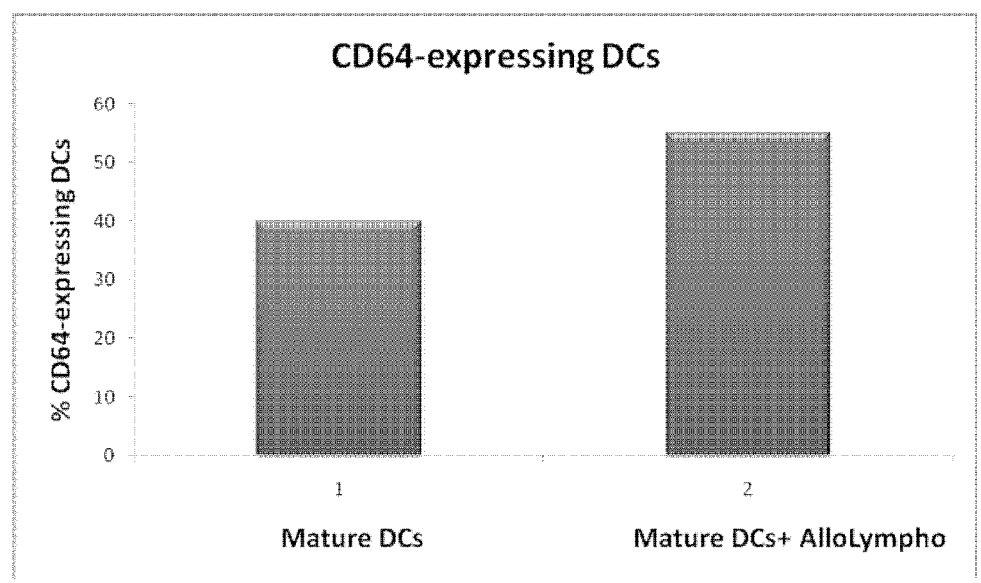
FIG. 12 illustrates that addition of irradiated ASALs to mature, monocyte-derived, DCs which are autologous with respect to the irradiated PBMCs used for priming of ASALs, enhance the number of DCs expressing CD64 which is the Fc-gamma receptor for anti-CD3 antibodies.

Results:

As shown in FIG. 12, addition of irradiated ASALs to irradiated, mature, monocyte-derived DCs, which are autologous with respect to the irradiated PBMCs used for priming of ASALs, enhance the number of CD64 (Fc-gammaR)-expressing DCs. This receptor is supposed to catch the Fc-part of soluble anti-CD3 antibodies. Such anti-CD3-"armed" DCs may then directly interact with and activate cocultured autologous or allogeneic CD3 expressing T cells.

Figure 13:
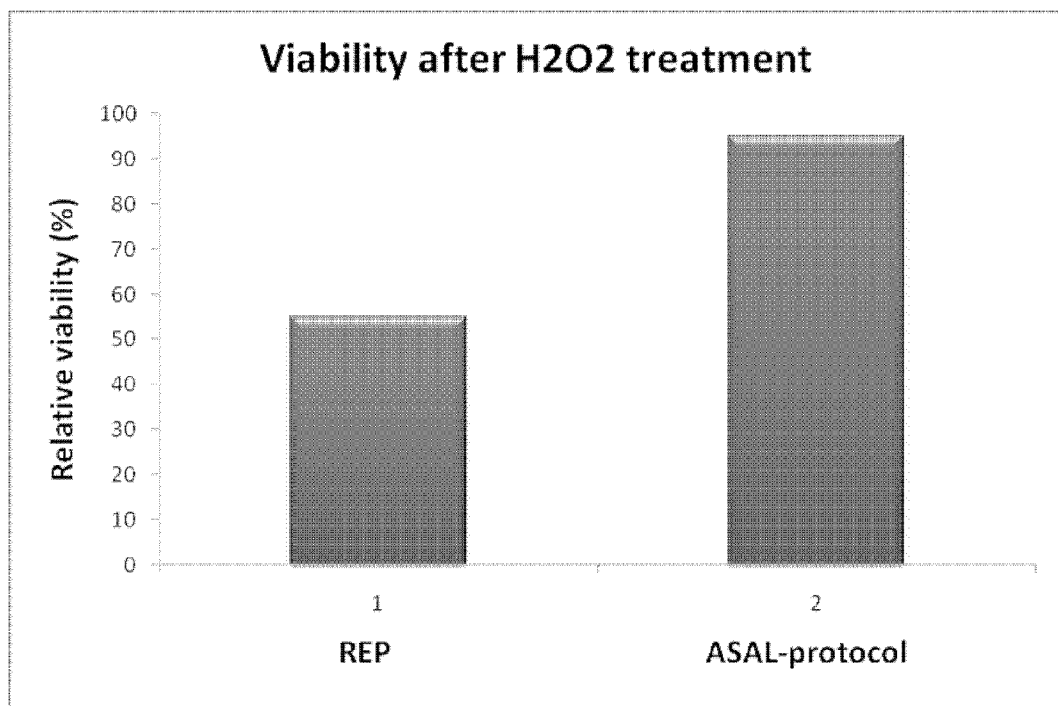
FIG. 13 illustrates that the ASAL protocol, in which CD3+ target T cells (non-transfected) are co-cultured and expanded with mature DCs and irradiated ASALs in medium supplemented with OKT3 (anti-CD3 antibody) and IL-2 for 12 days, induce T cells that are more resistant to apoptosis-inducing $H_2O_2$ treatment as compared to T cells expanded with the REP protocol

FIG. 13 shows the viability after $H_2O_2$ treatment. The ASAL protocol induces T cells that are more resistant to apoptosis-inducing $H_2O_2$ treatment as compared to T cells expanded with the REP protocol. Since $H_2O_2$ is a well-known immunosuppressing factor within tumors it may be expected that the ASAL protocol will expand T cells with a superior resistance to tumor-derived $H_2O_2$ in vivo.

Figure 14:
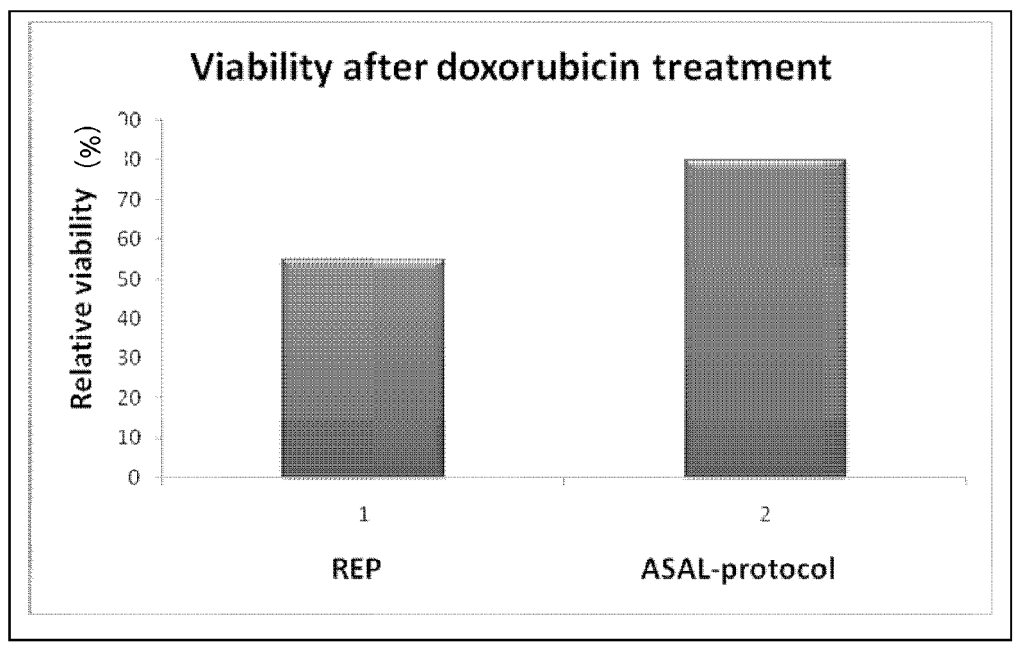
FIG. 14 illustrates that the ASAL protocol, in which CD3+ target T cells (non-transfected) are co-cultured and expanded with mature DCs and irradiated ASALs in medium supplemented with OKT3 (anti-CD3 antibody) and IL-2 for 12 days, induce T cells that are more resistant to apoptosis-inducing doxorubicin treatment as compared to T cells expanded with the REP protocol.
Figure 15:
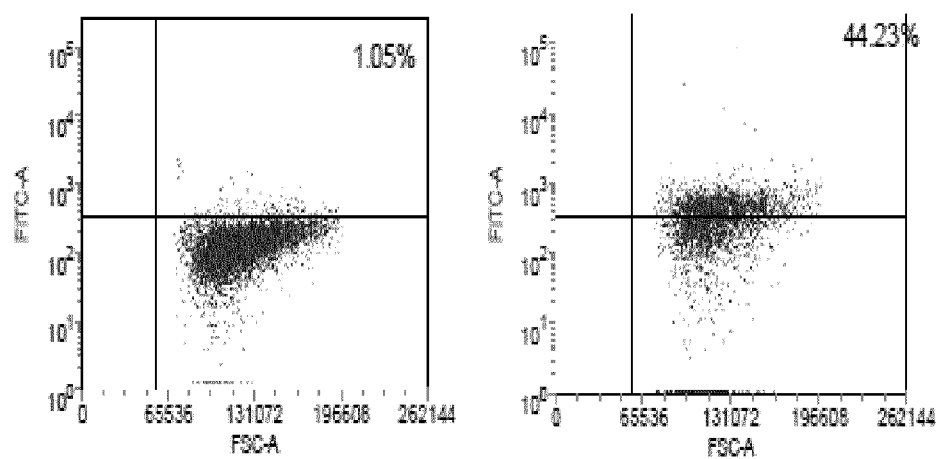
FIG. 15 illustrates efficient lentiviral transfection of CD3+ T cells (>40% transfected cells) with a chimeric antigen receptor (CAR) against the GD2 antigen expressed on glioblastoma cancer cells

FIG. 14 shows the viability after doxorubicin treatment. The ASAL protocol induces T cells that are more resistant to apoptosis-inducing doxorubicin treatment as compared to T cells expanded with the REP protocol. Since doxorubicin is a frequently used anti-cancer drug it may be expected that the ASAL protocol will expand T cells with a superior resistance to apoptosis induced by concurrent anti-cancer treatment with doxorubicin in vivo CD3+ T cells are efficiently transfected (>40% transfected cells) with a chimeric antigen receptor (CAR) against the GD2 antigen (expressed on glioblastoma cancer cells) (see FIG. 15). Left figure=before transfection, right figure after transfection. All dots within the upper right quadrant represent CAR-transfected T cells.

Figure 16:
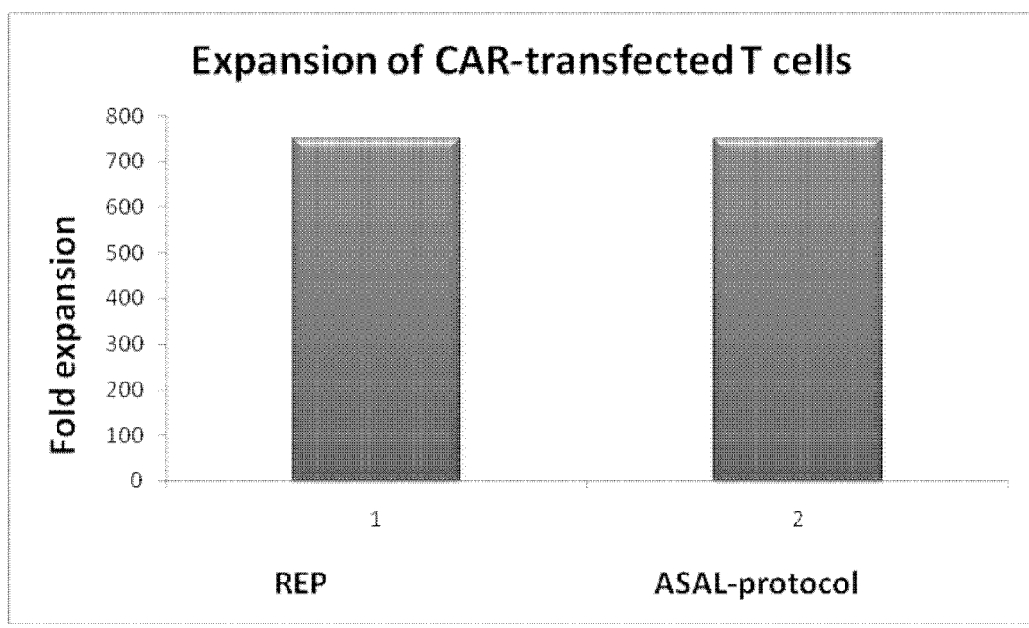
FIG. 16 illustrates that the ASAL protocol induce a similar expansion of CAR-transfected CD3+ T cells as compared to the standard REP protocol.
Figure 17:
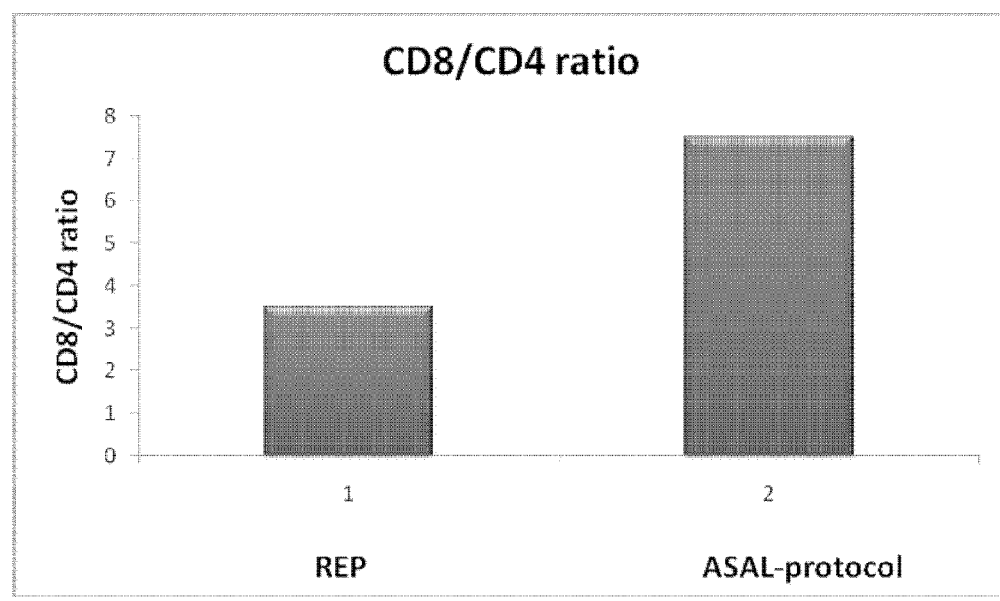
FIG. 17 illustrates that the ASAL protocol preferentially expands CAR-transfected CD8+ T cells as compared to the REP protocol.

The ASAL protocol induces a similar expansion of CAR-transfected CD3+ T cells as compared to the standard REP protocol (see FIG. 16), but expands CD8+ T cells at a higher ratio as compared to the REP protocol (see FIG. 17). This finding is of clinical significance since expansion protocols that favor expansion of CD4+ T cells are expected to compromise in vivo anti-tumor efficacy (Yang et al. Journal of Immunotherapy 2010; 33:648)

Figure 18:
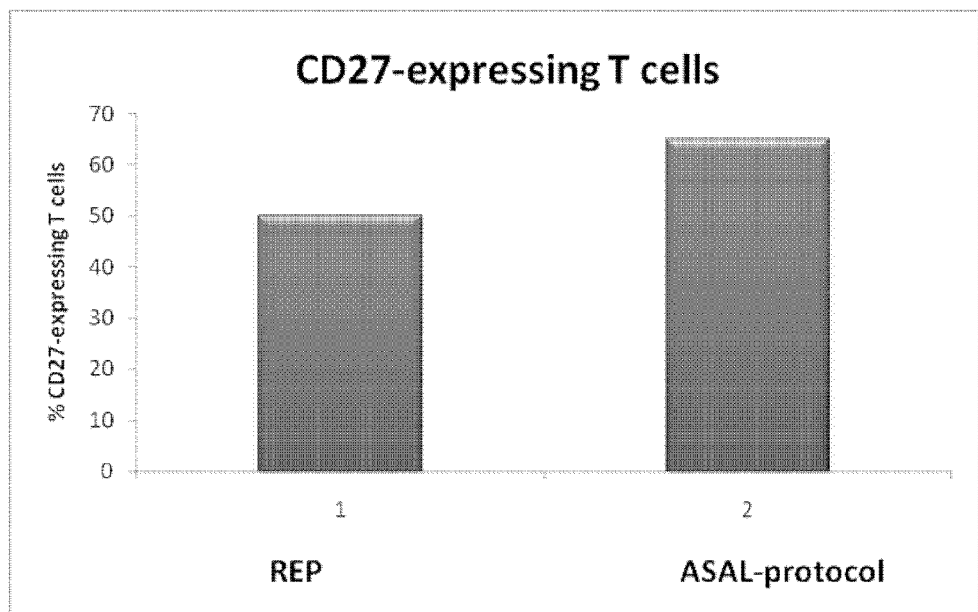
FIG. 18 illustrates that the ASAL protocol induce a similar or higher number of CD27-expressing CAR-transfected CD3+ T cells as compared to the REP protocol.

Further, the ASAL protocol induce a similar or higher number of CD27-expressing CD3+ T cells as compared to the REP protocol (see FIG. 18). This finding is clinically relevant since the persistence of T cells following adoptive transfer in humans has been shown to be directly correlated to high levels of CD27 expression on the reinfused T cells. $CD27^+$ $CD8^+$ T cells represent potentially more effective CTLs (cytotoxic T cells) for adoptive immunotherapy since they can provide an antigen-driven autocrine signal for proliferation. Such helper-independent CD8+ T cells would not require exogenous help in the form of IL-2 or $CD4^+$ T cells to survive and expand.

Figure 19:
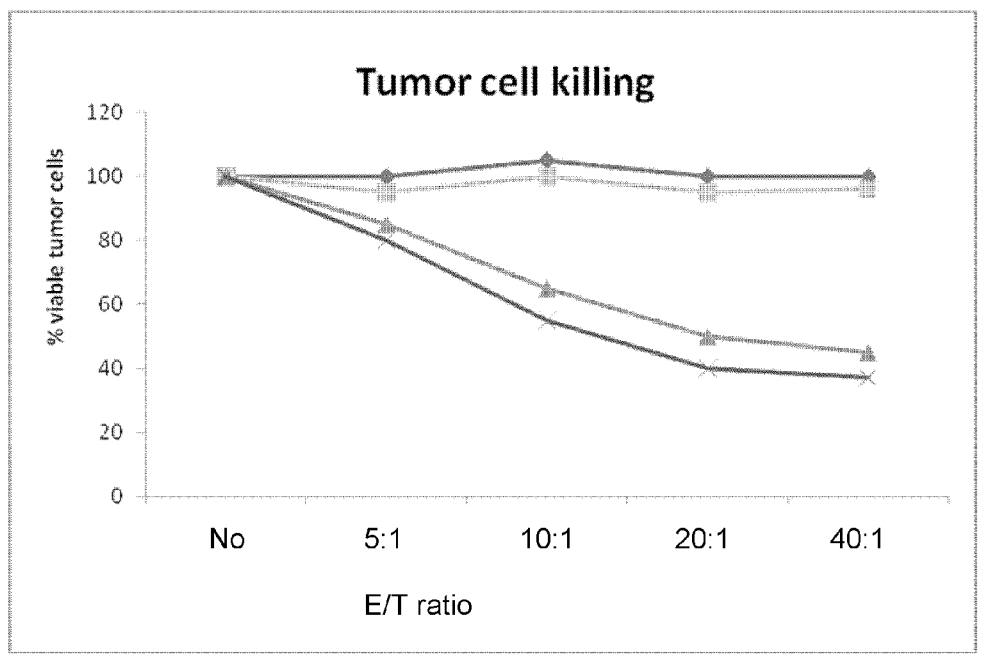
FIG. 19 illustrates that the ASAL protocol expands CAR-transfected T cells with a specific killing ability of GD2-expressing tumor cells that is similar to the specific killing ability of CAR-transfected T cells expanded with the REP protocol. Irrelevant T2 cells were used as control targets. Diamond (♦)=REP vs. GD2-negative targets; quadrant (■)=ASAL vs. GD2-negative targets; triangle (▲)=REP vs. GD2-expressing target cells; Cross (X)=ASAL vs. GD2-expressing targets.

As shown in FIG. 19, the ASAL protocol expand CAR-transfected T cells with a specific killing ability that is similar to the specific killing ability of CAR-transfected T cells expanded with the REP protocol.

Figure 20:
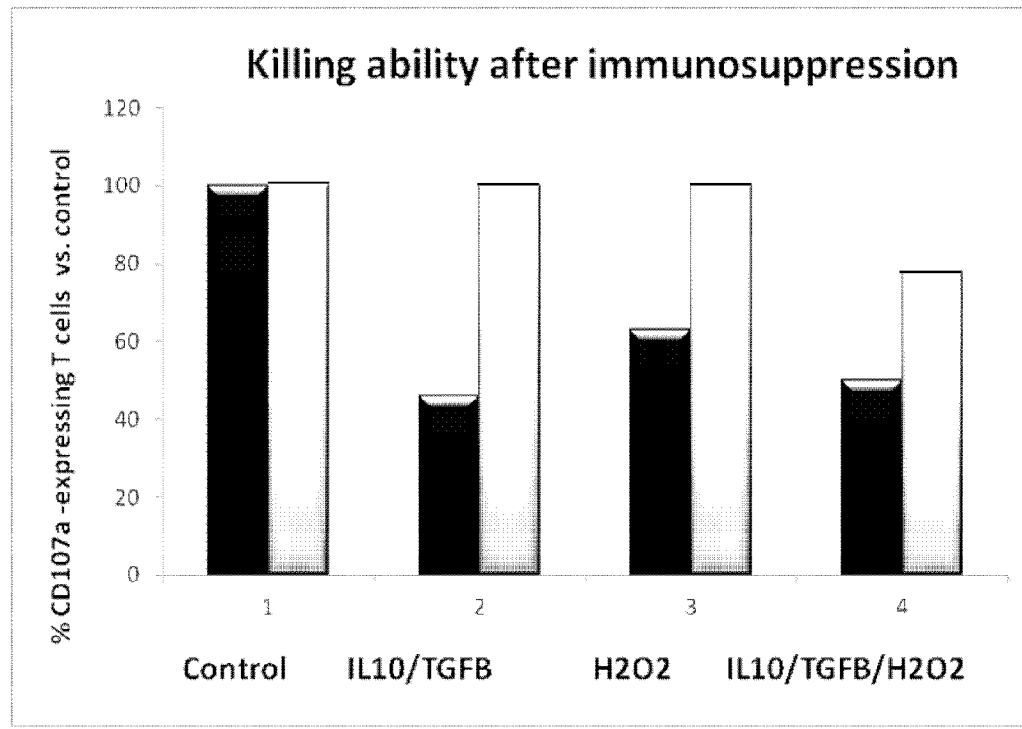
FIG. 20 illustrates that the tumor-specific cytotoxic activity in CAR-transfected T cells, as measured by membrane expression of CD107a (marker of lytic granule exocytosis), is more resistant to potential tumor-derived suppressive factors (IL-10, TNF-beta and/or $H_2O_2$) when the CAR-transfected T cells have been expanded with the ASAL protocol as compared with CAR-transfected T cells expanded with REP protocol. Black column=T cells expanded with REP; White column=CAR transfected T cells expanded with the ASAL protocol.
Figure 21:
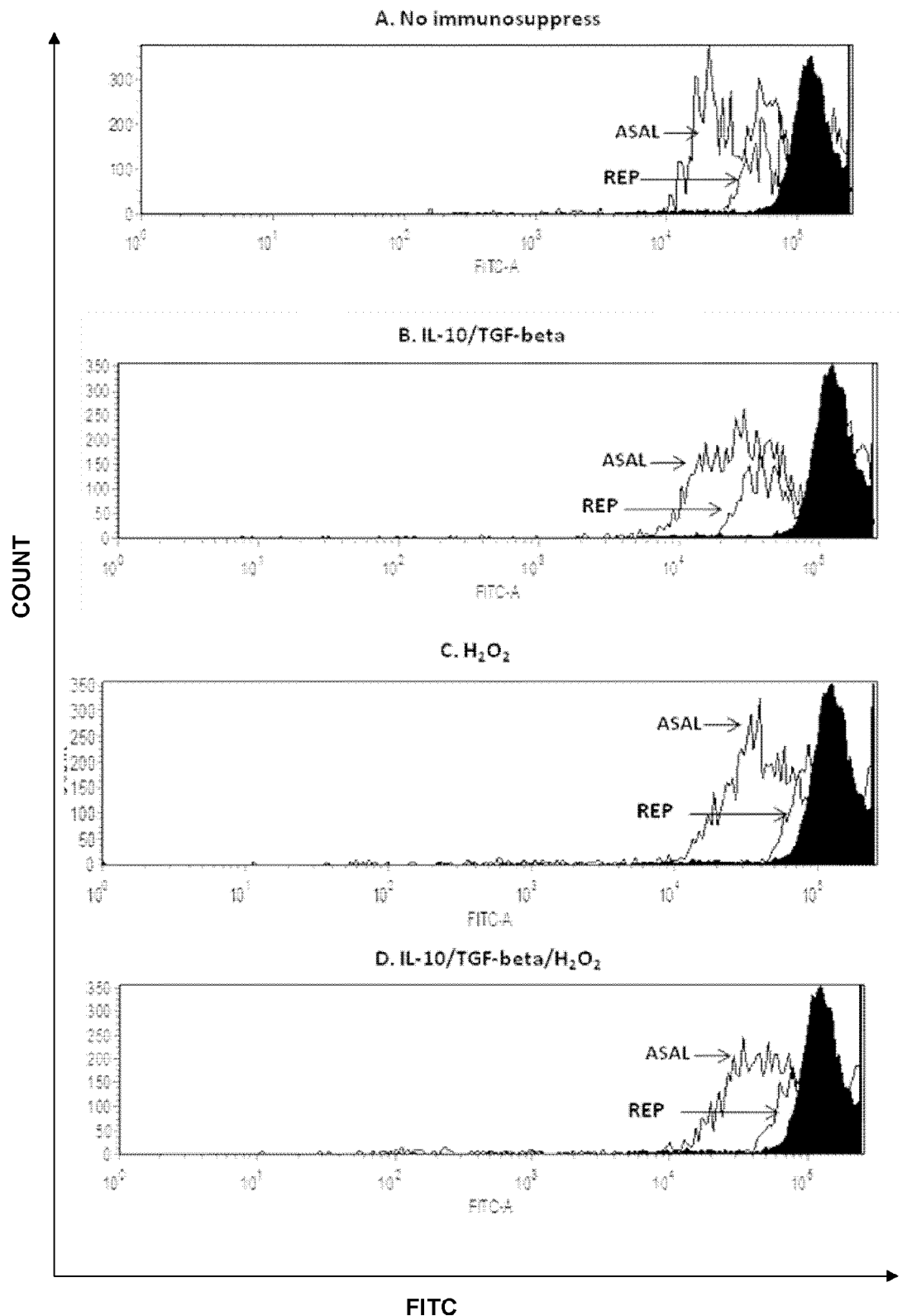
FIG. 21 illustrates that proliferative response of CAR-transfected T cells, after interaction and killing of target cells, is higher and more resistant to exposure to potential tumor-derived suppressive factors when compared to CAR-transfected T cells that have been expanded with REP protocol. A. No immunosuppressant; B: IL-10/TGF-beta treatment; C. $H_2O_2$ treatment; D: IL-10/TGF-beta and $H_2O_2$ treatment

The tumor-specific cytotoxic capacity in CAR-transfected T cells (as measured by membrane expression of CD107a) is more resistant to exposure of potential tumor-derived suppressive factors (IL-10, TNF-beta and/or $H_2O_2$) when the CAR-transfected T cells have been expanded with the ASAL-protocol as compared with CAR transfected T cells expanded with REP protocol (see FIG. 20).

The proliferative response of CAR transfected T cells, after interaction and killing of target cells, is higher and more resistant to potential tumor-derived suppressive factors when compared to CAR transfected T cells that have been expanded with REP protocol (a protocol frequently used to expand T cells; see Yang et al, Journal of Immunotherapy 2010; 33:648). Thus, after killing of target cells the T cells generated by the inventive method are re-stimulated and may therefore attack and kill new cancer cells Although particular embodiments have been disclosed herein in detail, this has been done by way of example for purposes of illustration only, and is not intended to be limiting with respect to the scope of the appended claims that follow. In particular, it is contemplated by the inventor that various substitutions, alterations, and modifications may be made to the invention without departing from the spirit and scope of the invention as defined by the claims.

The invention claimed is:

1. An in vitro method for priming of genetically modified antigen specific CD4+ and/or CD8+ T cells suitable for administration to a patient having a tumor, said method comprising co-culturing tumor antigen receptor expressing target T cells from the patient to be treated, mature dendritic cells, anti-CD3 antibodies and lymphocytes that have been sensitized against MHC class I and/or MHC class II antigens on antigen presenting cells (APCs), wherein the sensitized lymphocytes are obtained by culturing non-proliferating APCs from a first healthy donor with peripheral blood mononuclear cells (PMBCs) from a second healthy donor.

2. The method according to claim 1, wherein the tumor antigen receptors are selected from T-cell receptors (TCRs) and chimeric antigen receptors (CARs).

3. The method according to claim 1, wherein said non-proliferating antigen presenting cells are selected from the group consisting of PBMCs and monocyte derived dendritic cells.

4. The method according to claim 1, wherein the mature dendritic cells are obtained by first culturing monocytes in a composition comprising GM-CSF and IL-4 for about 1-7 days to obtain immature dendritic cells and subsequently adding a second composition that enables the immature dendritic cells to become mature dendritic cells by culturing for at least about 12 hours.

5. The method according to claim 4, wherein the second composition comprises TNF alfa, IL-1 beta, interferon gamma, interferon alpha or interferon beta and a TLR3 ligand.

6. The method according to claim 4, wherein the second composition comprises TNF alfa, interferon gamma, a TLR 3 ligand and/or a TLR 4 ligand, and a TLR7 agonist and/or a TLR 8 agonist.

7. The method according to claim 6, wherein the TLR 3 ligand is poly-1:C and the TLR 8 agonist is R848.

8. The method according to claim 1, wherein the cells are cultured for about 4 to 20 days.

9. The method according to claim 1, wherein exogenous IL-2, IL-7, IL-15, anti-IL-4 and/or IL-21 are added to the cell culture.

10. The method according to claim 1, wherein the primed antigen specific CD4+ and/or CD8+ T cells are restimulated by culturing said cells together with new dendritic cells, anti-CD3 antibodies, new sensitized allogeneic lymphocytes and optionally addition of exogenous IL-2, IL-7, IL-15, anti-IL-4 and/or IL-21 to the cell culture.

11. The method according to claim 4, wherein the TLR3 ligand comprises poly-1:C.

12. The method according to claim 1, wherein the non-proliferating APCs are autologous with respect to the mature dendritic cells.

13. The method according to claim 1, wherein the non-proliferating APCs are irradiated peripheral blood mononuclear cells (PMBCs).

* * * * *